United States Patent [19]
Carey

[11] Patent Number: 5,952,497
[45] Date of Patent: Sep. 14, 1999

[54] N$^\alpha$-BPOC AMINO ACID PENTAFLUOROPHENYL (PFP) ESTERS AND 3,4-DIHYDRO-4-OXO-1,2,3-BENZOTRIAZIN-3-YL (ODHBT) ESTERS

[75] Inventor: Robert I. Carey, Augusta, Ga.

[73] Assignee: University of Georgia Research Foundation, Athens, Ga.

[21] Appl. No.: 08/891,676

[22] Filed: Jul. 10, 1997

Related U.S. Application Data

[60] Provisional application No. 60/021,499, Jul. 10, 1996.

[51] Int. Cl.$^6$ .................. C07D 253/08; C07C 229/00
[52] U.S. Cl. ............................. 544/183; 560/19
[58] Field of Search .................... 511/243, 534; 544/183; 560/19

[56] References Cited

U.S. PATENT DOCUMENTS

| | | | |
|---|---|---|---|
| 4,192,798 | 3/1980 | Verlander et al. | 260/112.5 R |
| 4,351,762 | 9/1982 | Verlander et al. | 260/112.5 R |
| 5,011,940 | 4/1991 | Urbach et al. | 548/452 |
| 5,233,044 | 8/1993 | Hudson | 548/110 |

OTHER PUBLICATIONS

Tikhonov et al, Chemical Abstracts 93:239,904e, p. 905, Dec. 22, 1980.
Shvachkin et al, Chemical Abstracts 94:175,510j, p. 773, May 25, 1981.
Kisfaludy, L. et al. (1973), "Die Verwendung von Pentafluorphenylestern bei Peptid–synthesen," *Ann. Chem.* 9:1421–1429.
Albericio, F., and Barany, G. (1987) "An acid–labile anchoring linkage for solid–phase synthesis of C–terminal peptide amides under mild conditions" *Int. J. Peptide Protein Res.* 30:206–216.
Atherton, E., and Sheppard, R.C. (1985) "Solid phase peptide synthesis using N$_\alpha$–Fluorenylmethyoxycarbonylamino acid pentafluorophenyl esters" *J. Chem. Soc. Chem. Comm.*, pp. 165–166.
Atherton, E., et al. (1988) "Peptide Synthesis. Part 12. 3,4–Dihydro–4–oxo–1, 2, 3–benzotriazin–3–yl Esters of Fluorenylmethoxycarbonyl Amino Acids as Self–indicating Reagents for Solid Phase Peptide Synthesis" *J. Chem. Soc. Perkin Trans.* 1:2887–2894.
Atherton, E., et al. (1988) "Peptide Synthesis. Part 10. Use of pentafluorophenyl esters of fluroenylmethoxycarboxyl amino acids in solid phase peptide synthesis" *Tetrahedron* 44:843–857.
Barany, G., et al. (1987) "Solid–phase peptide synthesis: a silver anniversary report" *Int. J. Peptide Protein Res.* 30:705–739.
Carey, R.I., et al. (1996) "Protection of asparagine and glutamine during N–Bpoc–based solid–phase peptide synthesis" *Int. J. Peptide Prot. Res.* 47(3):209–213.
Colombo, R. (1981) "Synthesis by an improved solid–phase method of a highly acidic peptide from mucleolar nonhistone protein C23" *Bioorg. Chem.* 10:219–232.
Feinberg, R.S., and Merrifield, R.B. (1972) "The synthesis of biphenylisopropyloxycarbonyl–amino acids salts" *Tetrahedron* 28:5865–5871.
Fotouhi, N., et al. (1989) "Peptide synthesis by prior thiol capture." *J. Org. Chem.* 54:2803–2817.
Fotouhi, N., et al. (1992) "Resolution of proline acylation problem for thiol capture strategy by use of a chloro–dibenzofuran template" *Int. J. Peptide, Protein Res.* 40:141–147.
Fotouhi, N. and Kemp, D.S. (1993) "Novel class of silicon––based protective groups for the side chain of tyrosine" *Int. Peptide Protein Res.* 41(2):153–161.
Galpin, I., et al. (1981) "Peptides–XXXXV. Synthesis of the 118–129 fragment of a lysozyme analogue" *Tetrahedron* 37(17):3037–3041.
Galpin, I., et al. (1979) "Peptides–XXXVI. Synthesis of the 27–37 fragment of a lysozyme analogue" *Tetrahedron* 35:2785–2790.
Galpin, I., et al. (1981) "Peptides–XXXXVI. Studies in the synthesis of an analogue of hen egg white lysozyme." *Tetrahedron* 37(17):3043–3050.
Guibe, F., et al. (1989) "Use of an allylic anchor group and of its palladium catalyzed hydrostannolytic cleavage in the solid phase synthesis of protected peptide fragments" *Tetrahedron Lett.* 30:2641–2644.
Hammond, G.S. and Reeder, C.E. (1958) "Benzyl tosylates. VI. The effects of phenyl as a substituent" *J. Am. Chem. Soc.* 80:573–575.
Hiskey, R.G., et al. (1972) "Sulfur–containing polypeptides. XVI. Synthesis of the A$^{14-21}$ Fragment of ovine insulin" *J. Org. Chem.* 37(15):2478–2483.
Hudson, D. (1990) "Methodological implications of simultaneous solid–phase peptide synthesis: a comparison of active esters" *Peptide Res.* 3(1):51–55.
Hudson, D. (1988) "Methodological implications of simultaneous solid–phase peptide synthesis: 1. Comparison of different coupling procedures" *J. Org. Chem.* 53:617–624.
Juhasz, A., and Bajusz, S. (1979) "A novel amide–protecting group" *Acta Chim. Acad. Sci. Hung.* 102(3):289–296.
Kamber, B.., et al. (1976) "Syntheses von humaninsulin. III. Aufbau des geschutzten zweikettigen fragments A(14–21)— B(17–30)" *Helv. Chim. Acta* 59(8):2830–2840.
Kemp, D.S. (1981) "The amine capture strategy for peptide bond formation–An outline of progress" *Biopolymers* 20:1793–1804.

(List continued on next page.)

*Primary Examiner*—Zinna Northington Davis
*Attorney, Agent, or Firm*—Greenlee, Winner & Sullivan, P.C.

[57] ABSTRACT

This invention relates to N$^\alpha$-Bpoc amino acid pentafluorophenyl (Pfp) esters and 3,4-dihydro-4-oxo-1,2,3-benzotriazin-3-yl (ODhbt) esters and side-chain protected derivatives thereof which are useful in peptide, polypeptide, and protein synthesis. The invention relates to the esters, their preparation and their use in peptide synthesis.

42 Claims, No Drawings

OTHER PUBLICATIONS

Kemp, D.S., and Carey R.I. (1993) "Synthesis of a 39–peptide and a 25–peptide by thiol capture ligations: observation of a 40–fold rate acceleration of the intramolecular O, N–acyl–transfer reaction between peptide fragments bearing only cysteine protective groups" *J. Org. Chem.* 58:2216–2222.

Kemp, D.S., et al. (1991) "Resolution of the histidine problem for thiol capture—synthesis of a 39–peptide" *Tetrahedron Let.* 32(25):2845–2848.

Kemp, D.S., et al. (1989) "Rational design of templates for intramolecular O, N–acyl–transfer via medium–sized cyclic intermediates derived from L–cysteine. Definition of an experimental maximum in effective molarity through the study of tunable templates" *J. Org. Chem.* 54:1589–1603.

Kemp, D.S., et al. (1988) Practical preparation and deblocking condition for N–x–(2–(p–biphenylyl)–2–propyloxycarbonyl)–amino acid (N–α–Bpoc–Xxx–OH) derivatives. *Int. J. Peptide Protein Res.* 31:359–372.

Kisfaludy, L., and Schon, I. April, 1983 "Preparation and applications of pentafluorophenyl esters of 9–fluorenylmethyloxycarbonyl amino acids for peptide synthesis" *Synthesis* pp. 325–327.

Koenig, W. and Geiger, R. (1970) "Eine neue Amid–Schutzgruppe" *Chem. Ber.* 103:2041.

Kovacs, J., et al. (1970) "Rates of racemization and coupling of cysteine active ester derivatives" *J. Chem. Soc. Chem. Comm.* 53–54.

Kovacs, J., et al. (1970) "Racemization of amino acids derivatives. Rate of racemization and peptide formation of cysteine active esters" *J. Org. Chem.* 35:1810–1815.

Kunz, H., and Dombo, B. (1988) "Solid phase synthesis of peptides and glycopeptides on polymeric supports with allylic anchor groups" *Angew. Chem. Int. Ed. Engl.* 27(5):711–713.

Mojsov, S., and Merrifield, R.B. "Solid phase synthesis of crystalline glucagon" (1981) *Biochemistry* 20:2950–2956.

Rosowsky, A., and Wright, J.E. (1989) "$N^e$–[[2–(Trimethylsilyl)ethoxyl]carbonyl] Derivatives of tri–L–lysine and Tetra–L–lysine as potential intermediates in the block poLymer synthesis of macromolecular drug conjugates" *J. Org. Chem.* 54:5551–5558.

Rosowsky, A., and Wright, J.E. (1983) "$N^w$–Alkoxycarbonylation of $_{\alpha,w}$–Diamino Acids with 2–(Trimethylsily)ethyl 4–Nitrophenyl Carbonate" *J. Org. Chem.* 48:1539–1541.

Schon, I., and Kisfaludy, L. Apr., 1986 "9–Fluorenylmethyl pentafluorophenyl carbonate as a useful reagent for the preparation of N–9–Fluorenylmethyloxycarbonylamino acids and their pentafluorophenyl esters" *Synthesis* pp. 303–305.

Shimonishi, Y., et al. (1962) "Studies on the synthesis of peptides containing glutamine as the c–terminal. I. Protection of amide–nitrogen with xanthyl group during peptide syntehsis" *Bull. Chem. Soc. Japan* 35:1966–1970.

Schwertner, E., et al. (1975) "Synthese einiger [2–(p–Biphenylyl)isopropyloxy carbonyl]–Aminosäurederivate" *Liebigs Ann. Chem.* pp.581–585.

Seitz, O., and Kuna, H. (1995) "A novel allylic anchor for solid–phase synthesis–synthesis of protected and unprotected O–glycosylated Mucin–type glycopeptides" *Angew. Chem. Int. Ed. Engl.* 34(7): 803–805.

Sieber, P. and Iselin, B. (1968) "Selektive acidolytsche Spaltung von Aralkyloxycarbonyl–Aminoschutzgruppen" *Helv. Chim. Acta* 51(4):614–622.

Sieber, P., and Iselin, B. (1968) "Peptidsynthesen unter verwendung der 2–(p–Diphenyl)–isopropyloxycarbonyl (Bpoc)–Aminoschutzgruppe" *Helv. Chim. Acta* 51(4):622–632.

Sieber, P., et al. (1977) "Totalsynthese von Humaninsulin. IV. Beschreibung der Endstufen" *Helv. Chim. Acta* 60:27–37.

Sieber, P. and Riniker, B. (1991) "Protection of carboxamide functions by the trityl residue application to peptide synthesis" *Tetrahedron Lett.* 32(6):739–742.

Trudelle, Y., and Heitz, F. (1987) "Synthesis and characterization of Tyr(Bzl) $^{9,11,13,15}$ and Tyr$^{9,11,13,15}$ gramicidin A" *Int. J. Peptide Protein Res.* 30:163–169.

Wang, S.S., and Kulesha, I.D. (1975) "Preparation of protected peptide intermediates for a synthesis of the ovine pituitary growth hormone sequence 96–135" *J. Org. Chem* 40(9):1227–1234.

Wang, S.S., and Merrifield, R.B. (1969) "Preparation of some new biphenylisopropyloxycarbonyl amino acids and their application to the solid phase synthesis of a tryptophan––containing heptapeptide of bovine parathyroid hormone" *J. Prot. Res.* 1:235–244.

Wang, S.S., et al. (1974) "Solid phase synthesis of bovine pituitary growth hormone–(123–131) nonapeptide" *Int. J. Peptide Protein Res.* 6:103–109.

Weygand, F., et al. (1968) "Vergleichende untersuchungen zur abspaltung substit. Benzylreste vom amidstidkstoff und deren kombinatiönsmoglichkeiten mit urethanschutzgruppen." *Chem. Ber.* 101:3623–3641.

Weygand, F., et al. (1969) "Easily cleavable protective groups for acid amide groups. II. Comparative studies on the cleavage of substituted benyzl groups from amide nitrogen and possible combinations of such radicals with urethane protective groups." *Chem. Abstracts,* entry 4567h, 70:446.

N$^\alpha$-BPOC AMINO ACID PENTAFLUOROPHENYL (PFP) ESTERS AND 3,4-DIHYDRO-4-OXO-1,2,3-BENZOTRIAZIN-3-YL (ODHBT) ESTERS This application claims the benefit of prior provisional application No. 60/021,499 filed Jul. 10, 1996.

FIELD OF THE INVENTION

This invention relates to N$^\alpha$-Bpoc-amino acid compounds (Bpoc=2-(p-biphenylyl)-propyloxycarbonyl), namely N$^\alpha$-Bpoc-amino acid pentafluorophenyl (Pfp) esters and N$^\alpha$-Bpoc-amino acid 3,4-dihydro-4-oxo-1,2,3-benzotriazin-3-yl (ODhbt) esters, their preparation and their use in peptide, polypeptide, and protein synthesis.

BACKGROUND OF THE INVENTION

The N$^\alpha$-Bpoc group, which was introduced by Sieber and Iselin in 1968 (1) has played a key role in the synthetic strategy used in several precedent-setting solution phase peptide syntheses of historical note, in particular the first total synthesis of human insulin (2,3) and in the total synthesis of an analog of hen egg white lysozyme (4). Bpoc amino acids have also been applied to solid phase peptide synthesis. Merrifield and Mojsov employed Bpoc amino acids in their solid phase synthesis of crystalline glucagon (6), and Kemp and coworkers have used Bpoc amino acids to do solid phase synthesis on a phenyl ester resin, preparing 4-(peptidyloxy)-6-mercaptodibenzofuran esters for use in thiol capture (9, 11, 12) ligations that have resulted in the completed syntheses of peptides of 25, 29, 34, and 39 amino acids in length. Other studies of solid phase synthesis with Bpoc-amino acids have resulted in the preparation of a nonapeptide from bovine pituitary growth hormone (13), a heptapeptide from bovine parathyroid hormone (14) tyrosine containing analogs of the ion-channel forming pentadecapeptide, Gramacidin A (15), and a 42-amino acid sequence corresponding to a highly acidic fragment of nucleolar nonhistone protein C23 (16).

In the work described above, the application of Bpoc amino acids to solid phase peptide synthesis was done by first preparing and storing the cyclohexyl- or dicyclohexylamine salts of each derivative, which then had to be liberated from the salt and activated prior to each coupling. Most of the Bpoc amino acids, as free acids, are obtained as oils which have a relatively short shelf-life. The oils undergo an autocatalytic decomposition to the amino acid, $CO_2$ and to the Bpoc olefin and its dimer with a half-life of weeks. Bpoc-Leu-OH and Bpoc-Asn-OH, which alone among the free acids, are obtained as crystalline solids, have a longer shelf-life of at least a year if kept dry at −20° C.

Certain active esters of Bpoc amino acids (usually hydroxysuccinimide, nitrophenyl, 2,3,5-trichlorophenyl, or pentachlorophenyl) were prepared and stored for use in the solution phase peptide syntheses listed above, but the esters used were not efficient enough to be practical for application to solid-phase synthesis.

The favorable properties of Pfp esters were noted by Kovacs, who in his study of N$^\alpha$-urethane-protected cysteine derivatives (20), identified Pfp esters as having the highest $k_{coup}/k_{rac}$ ratio of a wide range of active esters studied. Kisfaludy (22) first prepared Pfp esters of Fmoc amino acids that were later applied by Atherton and Sheppard (24) to solid phase synthesis in their Fmoc/polyamide continuous flow system. In a recent comprehensive study, Hudson (26) has reported simultaneous competition and comparison methods to evaluate the activities of twenty-six reactive esters of N$^\alpha$-Fmoc protected amino acids. Pfp esters were identified as being the most suitable selection for routine use in solid-phase synthesis.

The in situ preparation of 3,4-dihydro-4-oxo-1,2,3-benzotriazin-3-yl (ODhbt) esters of certain urethane protected amino acids was disclosed by König and Geiger (43), but did not gain favor due to the formation of an o-azidobenzoic acid ester as a by-product of their preparation. Atherton and Sheppard (24) demonstrated the usefulness of pre-formed ODhbt esters of Fmoc-amino acids, if they were first crystallized and obtained in a homogeneous state free of the azido impurity formed in the in situ preparation.

A recent review of solid-phase peptide synthesis is provided in Barany, G. et al.(47) This reference is specifically incorporated by reference in its entirety herein to provide details of solid-phase synthetic methods.

The present work relates to Pfp and ODhbt activated esters of N$^\alpha$-Bpoc amino acids, particularly those that are crystalline, which have apparently not been reported previously.

SUMMARY OF THE INVENTION

It is an object of the invention to provide Bpoc-Xxx-Pfp esters and Bpoc-Xxx-ODhbt esters, (where Xxx represents any derivatized or non-derivatized amino acid) of amino acids particularly those commonly used in peptide, polypeptide, and protein synthesis. In addition, this invention provides Bpoc-Xxx-Pfp amino acid esters and Bpoc-Xxx-ODhbt amino acid esters in which the side group(s) of the amino acid carries a protective group. Preferred side group protecting groups are those that are removed under conditions distinct from those used to remove the Bpoc group, i.e., typically 0.5% TFA.

Another object of the invention is to provide procedures for the preparation of substantially pure, crystalline, stable Bpoc-Xxx-Pfp esters and Bpoc-Xxx-ODhbt esters of the amino acids.

Yet another object of the invention is to provide an improved method for the synthesis of peptides and polypeptides preferably utilizing substantially pure, crystalline Bpoc-Xxx-Pfp esters and/or Bpoc-Xxx-ODhbt esters and their side chain protected derivatives. This synthesis offers the following major advantages over conventional methods of polypeptide synthesis:

(1) N$^\alpha$-Bpoc amino acid Pfp esters and N$^\alpha$-Bpoc amino acid ODhbt esters of this invention include stable, storable, crystalline materials, as well as stable, storable amorphous solids and, therefore, facilitate and simplify both solid and solution phase peptide synthesis, especially in automated peptide synthesizers, by eliminating the need for activations, filtrations, and couplings prior to the peptide bond forming reaction. The purification of peptides prepared in solution is greatly facilitated by the use of these compounds because of the substantial lack of by-products produced by coupling agents.

(2) N$^\alpha$-Bpoc amino acid Pfp esters and N$^\alpha$-Bpoc amino acid ODhbt esters can be used in combination with resin linkages (e.g., oxime, phenyl ester, thioester, allyl ester, p-hydroxybenzyl ester and PAL linkers, that are not stable to the repetitive basic reagents (typically 20% piperidine in DMF) used to remove N$^\alpha$-Fmoc groups.

(3) N$^\alpha$-Bpoc amino acid Pfp esters and N$^\alpha$-Bpoc amino acid ODhbt esters can be used in combination with side-chain protecting groups and resin-linkages that are removable with trifluoroacetic acid/scavenger mixtures, distinguishing them from analogous $N^{\alpha}$-Boc derivatives that require side-chain protecting groups and resin-linkages that are removable only with stronger acid (e.g., HF or trifluoromethanesulfonic acid)/scavenger mixtures.

(4) $N^{\alpha}$-Bpoc amino acid Pfp esters and $N^{\alpha}$-Bpoc amino acid ODhbt esters provide, after coupling, the $N^{\alpha}$-Bpoc urethane protecting group on the amino function of the growing peptide chain which may then be removed by 0.5% (or lower concentration) TFA solvent mixtures, distinguished from the more concentrated TFA solvent mixtures necessary for removal for an $N^{\alpha}$-Bpoc group. The selectivity for the removal with 0.5% TFA for Bpoc/Boc is 3000:1.

(5) $N^{\alpha}$-Bpoc amino acid Pfp esters and $N^{\alpha}$-Bpoc amino acid ODhbt esters will greatly facilitate peptide synthesis with $N^{\alpha}$-Bpoc amino acids in comparison to the use of $N^{\alpha}$-Bpoc amino acid cyclohexylamine or dicyclohexylamine salts, which require tedious manipulation to activate the storage stable salts for peptide couplings.

(6) $N^{\alpha}$-Bpoc amino acid Pfp esters and $N^{\alpha}$-Bpoc amino acid ODhbt esters will greatly facilitate peptide synthesis with $N^{\alpha}$-Bpoc amino acids in comparison to the use of other $N^{\alpha}$-Bpoc amino acid active esters (e.g., hydroxysuccinimide, pentachlorophenyl, 2,3,5-trichlorophenyl, or p-nitrophenyl) whose reactivity is too sluggish to be useful in practical application to solid-phase peptide synthesis.

This invention provides amino acid Pfp esters and amino acid ODhbt esters of the general formula:

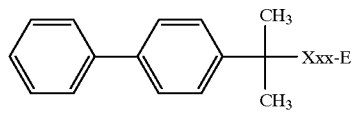

where E represents the ester moieties:

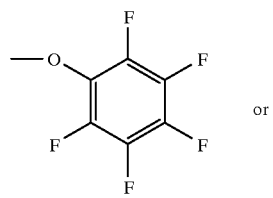

or

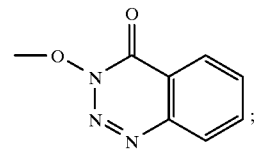

Xxx represents an amino acid, including a side group-protected amino acid.

$N^{\alpha}$-Bpoc amino acid Pfp esters and $N^{\alpha}$-Bpoc amino acid ODhbt esters of this invention include those of the general structures:

Formula I

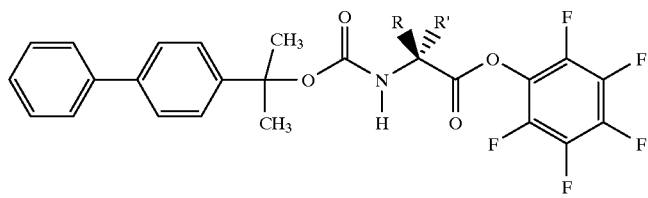

Formula II

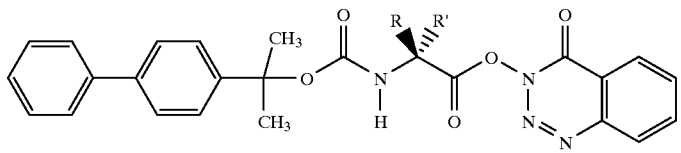

where R and R' most generally are any of the side groups of amino acids commonly used in peptide synthesis, including protected side groups commonly employed in peptide synthesis. More specifically, R and R' are selected from hydrogen, alkyl, cycloalkyl, substituted alkyl, substituted cycloalkyl, aryl, or substituted aryl. Substituted alkyl, substituted cycloalkyl and substituted aryl include substitution with halogens and noncarbon atoms, for example, in heterocyclic alkyl and aryl groups, particularly those substitutions found in naturally occurring amino acids, including those amino acids found in peptides.

This invention includes those esters of formula I and II in which one of R or R' is H and the other is the side chain on the α-carbon atom of an amino acid such as glycine, alanine, valine, leucine, isoleucine, proline, arginine, lysine, histidine, serine, threonine, aspartic acid, glutamic acid, asparagine, glutamine, cysteine, cystine, methionine, ornithine, norleucine, phenylalanine, tyrosine, tryptophan, β-alanine, homoserine, homoarginine, isoglutamine, pyroglutamic acid, γ-aminobutryic acid, citrulline, sarcosine, statine and the like, including derivatives with appropriate side group protection.

The R and R' side chains of the amino acid may be protected as required, using common techniques and protecting groups well known to one skilled in the art, such as the commonly employed amino, hydroxy, thiol and carboxy protecting groups. Preferred side-chain protecting groups are those that are removed under conditions distinct from that of the Bpoc group. More preferred side-chain protecting groups for the compounds of this invention are t-butyl-type and benzyl-type groups. For use herein, a t-butyl-type protective group includes those protective groups with similar deprotection chemistry as a t-butyl group, i.e., those protective groups that will be removed in approximately the same time as a t-butyl group, in acidolytic deprotection mixture.

Similarly, for use herein, a benzyl-type group includes those protective groups that will be removed in approximately the same time as a benzyl group, in acidolytic deprotection mixture.

The compounds of this invention also include those of formula I and II in which both R and R' are side chains attached to the α-carbon of an amino acid as, for example, in the case of isovaline where one of R or R' is ethyl and the other is methyl.

The compounds of the invention also include esters of formula I and II wherein carbon atoms from the R or R' groups are part of a cyclic ring such as ortho-amino benzoic acid or 1-amino-2-carboxy cyclohexane.

As indicated in formulas I and II and as appreciated in the art, amino acids may be optically active. (Those in which R and R' are the same are not optically active.) In most cases, L-amino acids (the form occuring in proteins) will be used in polypeptide synthesis. The activated, N-protected amino acids of this invention can, however, be optically active in either the L- or D-form, including mixtures of enatiomers in which one form is in excess, or racemic mixtures of enantiomers.

The invention also includes the improvement in the synthesis of a polypeptide chain wherein an N-protected amino acid component is deprotected and the deprotected amino acid component is allowed to react with a second, similar or dissimilar, activated N-protected amino acid component and the process repeated until the desired polypeptide is obtained, said improvement comprising using as the activated N-protected amino acid component in at least one of said reactions a compound having the structure of Formula I or II where R and R' are defined above.

Yet another aspect of the invention involves an improvement in the solid phase synthesis of a polypeptide chain on an insoluble solid support wherein an N-protected amino acid component is coupled by condensation reaction to an insoluble solid support containing substituent groups reactive with the carboxyl terminus end of said amino acid component, the coupled N-protected amino acid component is deprotected, a second similar or dissimilar activated N-protected amino acid component is coupled to said deprotected amino acid compound, and the process repeated until the desired polypeptide is obtained, said improvement comprising using as the activated N-protected amino acid component in at least on the said reactions a compound having the structure of formula I or II wherein R and R' are defined above. Preferred solid-phase methods of this invention are those in which the conditions for removal of the Bpoc groups, side-chain protecting groups and for cleavage of the resin linkage are substantially orthogonal, i.e., substantially distinct.

DETAILED DESCRIPTION OF THE INVENTION

The term "substantially pure" as used herein with respect to Bpoc amino acid esters relates to preparation of these esters substantially free of contaminating by-products or side-products that would significantly interfere with their use in solid or solution phase peptide synthesis. Substantially pure materials may, for example, be obtained in crystalline form. Preferably they are prepared substantially free of undesired racemization products or decomposition products. The term "substantially pure" as used herein with respect to peptides, including polypeptides and proteins, relates to preparation of peptides substantially free of the products of undesired side group reactions and undesired by-products including those produced by coupling reagents.

The use of the Bpoc reagents of this invention facilitate purification of peptides, synthesized by solid-phase and solution methods using them, due to the reduced generation of by-products and side-products of reaction.

The reagents, Bpoc-phenyl carbonate, Bpoc-azide, and Bpoc-p-methoxycarbonyl-carbonate, which serve as starting materials for the preparation of Bpoc-amino acid Pfp esters and Bpoc-amino acid ODhbt esters can be prepared by a number of procedures known to one skilled in the art. See for example Sieber and Iselin, (1); Feinberg and Merrifield, (29); Kemp, et al., (28).

Pentafluorophenyl esters can be prepared by a number of procedures well-known to one skilled in the art. See for example, Kovacs, et al., (20); Kisfaludy and Schön (22); or Atherton, et al., (24). Most often this preparation is accomplished through the reaction of the N-protected amino acid with a condensing agent (e.g., dicyclohexylcarbodiimide) in the presence of pentafluorophenol in a suitable solvent, tetrahydrofuran, ethyl acetate, dioxane, dimethoxyethane. Usually the reaction is carried out at 0° C., but some side-chain protected derivatives are best prepared at lower temperatures −10° C. to −30° C. The syntheses and certain properties of a number of Bpoc-Xxx-OPpf esters are described in the Examples.

3,4-Dihydro-4-oxo-1,2,3-benzotriazin-3-yl esters can be prepared by a number of procedures well known to one skilled in the art. See for example König and Geiger, (43), or Atherton et al., (46). Most often this preparation is accomplished through the reaction of the N-protected amino acid with a condensing agent (e.g., dicyclohexylcarbodiimide) in the presence of 3,4-dihydro-3-hydroxy-4-oxo-1,2,3-benzotriazine in a suitable solvent, tetrahydrofuran, ethyl acetate, dioxane, dimethoxyethane. Usually the reaction is carried out at 0° C., but some side-chain protected derivatives are best prepared at lower temperatures −10° C. to −50° C. Exemplary synthesis of ODhbt esters are provided in the Examples. Table 1 provides a summary of certain properties of Bpoc ODhbt esters.

While urethanes in general can be used as protecting groups for nucleophilic atoms, only a few have found widespread use in peptide synthesis, for example, t-butyloxycarbonyl (Boc); benzyloxycarbonyl (Cbz); and 9-fluorenyloxycarbonyl (Fmoc), and only the Boc and Fmoc amino acids have found widespread use in solid-phase peptide synthesis. Bpoc-amino acids were investigated early for application to solid-phase peptide synthesis, but did not gain widespread use for the following reasons: (1) Bpoc-amino acids, which are not stable to storage as the free acid, were traditionally stored as cyclohexylamine or dicyclohexylamine salts, requiring time-consuming manipulation prior to each coupling in solid-phase peptide synthesis. (2) Suitable strategies for side chain protection were not worked out for the common trifunctional amino acids, causing numerous side-reactions and resulting in impure products. Bpoc-amino acid Pfp and ODhbt esters are stable to storage, and are thus of particular interest for solid phase peptide synthesis. Accordingly, Bpoc-amino acid Pfp and ODhbt esters of side-chain protected amino acid derivatives that are suitable for solid-phase peptide synthesis with repetitive removal of the $N^\alpha$-Bpoc group are very useful compounds.

Bpoc-amino acid Pfp and ODhbt esters can be prepared by reaction of an amino acid derivative with a suitably reactive 2-(p-biphenylyl)-propyloxycarbonyl derivative of the following structure:

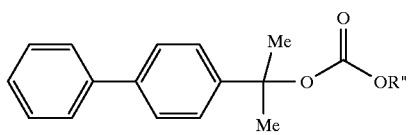

where R"=phenyl, p-methoxycarbonylphenyl, or any halide, aryl, substituted aryl, alkyl, substituted alkyl, or where OR is replaced by azide, $N_3$. The resulting $N^\alpha$-Bpoc amino acid is then immediately esterified with a suitable condensing agent (e.g., dicyclohexylcarbodiimide) in the presence of pentafluorophenol or 3,4-dihydro-3-hydroxy-4-oxo-1,2,3-benzotriazine as described above and as described in detail in Examples I, II, III, and XXXII.

As a result of the discoveries listed herein, virtually any Bpoc-amino acid Pfp or ODhbt ester, prepared from any starting amino or protected amino acid derivative, may be prepared easily in high yield with only minimal precaution for exclusion of moisture. The process is readily scaled up and can provide products which are highly crystalline, are readily purifiable by simple techniques (i.e., crystallization), and/or are stable to storage. Although it is recommended that these derivatives be stored at −20° C. in a dry container (where they are completely stable for a year and probably longer), they may be weighed, shipped, and stored for use in peptide synthesis under typical ambient laboratory conditions without fear of decomposition.

Of Bpoc-amino acid Pfp esters typically used in peptide synthesis, only that of serine was found not to be isolated as a storage stable solid. Most were isolated as crystalline materials. Bpoc-Glu(tBu)-Pfp was isolated as an amorphous solid at RT, but could be isolated as crystals at low temperature. This amorphous solid is storage stable. It is important to note that Bpoc-Ser-ODhbt is crystalline. Bpoc-Glu(tBu)-ODhbt was also a storage stable amorphous solid. Thus, a full complement of storage stable amino acid synthesis reagents is provided with the combination of the Bpoc-Pfp and ODhbt esters.

An advantage of the use of Bpoc-amino acid Pfp or ODhbt esters is that they allow a strategy of peptide synthesis in which the growing peptide is subjected neither to concentrated base (as in the aforementioned Fmoc strategy) nor to concentrated or strong acid (as in the aforementioned Boc strategy). The use of the title compounds described herein offer all the advantages of previously described Bpoc-amino acid derivatives, but without the disadvantages (storage as primary or secondary amine salts, storage as free acids, sluggish reactivity of poorly reactive esters) that have made previously prepared Bpoc-amino acid derivatives not commercially suitable for peptide synthesis. Thus, the invention provides storable, yet highly reactive, pre-activated reagents, which yield minimal side products during peptide bond formation. The invention is readily adapted to existing commercial instrumentation for peptide synthesis since it incorporates widely accepted, well-understood urethane protection for the amine function and widely accepted, well understood activation for the carboxy function for peptide bond formation. The solvents, conditions, and programming times need only be adapted for a Bpoc strategy.

Storage stable Bpoc esters of this invention include: Bpoc-Gly-Pfp, Bpoc-Ala-Pfp, Bpoc-Arg(Pmc)-Pfp, Bpoc-Val-Pfp, Bpoc-Leu-Pfp, Bpoc-Ile-Pfp, Bpoc-Pro-Pfp, Bpoc-Met-Pfp, Bpoc-Phe-Pfp, Bpoc-Trp-Pfp, Bpoc-Try(allyl)Pfp, Bpoc-Glu(tBu)-Pfp, Bpoc-Asn(Trt)-Pfp, Bpoc-Asp(tBu)-Pfp, Bpoc-Gln(Trt)-Pfp, Bpoc-Thr(tBu)-Pfp, Bpoc-Lys(Tfa)-Pfp, Bpoc-His(Trt)-Pfp, Bpoc-Cys(tButhio)-Pfp, Bpoc-Gly-ODhbt, Bpoc-Ala-ODhbt, Bpoc-Arg(Pmc)-ODhbt, Bpoc-Val-ODhbt, Bpoc-Leu-ODhbt, Bpoc-Pro-ODhbt, Bpoc-Phe-ODhbt, Bpoc-Trp-ODhbt, Bpoc-Trp-ODhbt, Bpoc-Try(allyl)ODhbt, Bpoc-Glu(tBu)-ODhbt, Bpoc-Asn(Trt)-ODhbt, Bpoc-Asp(tBu)-ODhbt, Bpoc-Gln(Trt)-ODhbt, Bpoc-Thr(tBu)-ODhbt, Bpoc-His(Trt)-ODhbt, Bpoc-Cys(tButhio)-ODhbt.

While the Bpoc-amino acid Pfp or ODhbt esters of the invention can be used in the synthesis of polypeptides by classical methods using a series of deprotection and coupling reactions, they are particularly well adapted for use in solid phase polypeptide synthesis. It should be understood that the term "polypeptides" as used herein is meant to include peptides, glycopeptide, depsipeptides, peptidomimetic molecules, and proteins. Also, it should be understood that the present invention contemplates sequential peptide synthesis wherein N-protected amino acids other than Bpoc-amino acid Pfp or ODhbt esters are employed as well as at least one Bpoc-amino acid Pfp or ODhbt ester of the invention. In practice, however, the N-protected amino acid component used in each sequence are preferably the Bpoc-amino acid Pfp or ODhbt esters of this invention.

A particular application of the $N^\alpha$-Bpoc esters of this invention is in solid-phase peptide synthesis using a phenyl ester-type resin, such as in Formula 4, using a resin with oxime or thioester linkages, or using resins containing an allyl ester-type linker (36) that is cleavable with a palladium catalyst Formula 4

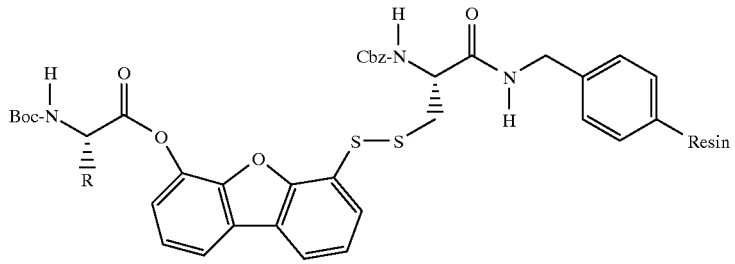

Although most solid-phase peptide synthesis is currently done by either using $N^\alpha$-Bpoc amino acids or $N^\alpha$-Bpoc amino acids, neither of these strategies is suitable for use with the phenyl ester- or allyl-type resins. The Fmoc strategy is incompatible because repetitive treatments with piperidine/DMF cleave the phenyl ester (or allyl) bond linking the peptide to the resin. The Boc strategy requires harsh acidolytic conditions (anhydrous HF or triflic acid/TFA mixtures) for global deprotection of all the side-chain protecting groups which is undesirable for many target molecules. The repetitive removal of the Bpoc group is compatible with a phenyl or allyl ester linkage on the solid-phase resin, and the strategy allows for mild acidolytic deprotection conditions of side chain protecting groups, such as tert-butyl-type side chain protecting groups, at the end of the synthesis.

Methods and compounds of this invention resolve several problems that arise in the use of side-chain protected Bpoc-amino acids in solid-phase synthesis, such as those that arise with side-chain protection of asparagine and glutamine. In previous solid-phase syntheses employing Bpoc-amino acids, asparagine and glutamine were coupled to the Bpoc group and the carboxamide side-chain function was left unprotected. These unprotected derivatives were found to have poor solubility properties, and in the case of asparagine, the special conditions required for coupling resulted in some cleavage of the growing peptide from a phenyl ester resin. (8–11) Another recurring problem is that, if left unprotected, the carboxamides of asparagine and glutamine can lead to resin-bound aggregation phenomena that limit the yield of coupling and deprotection steps in routine solid-phase synthesis. In one case of solid-phase peptide synthesis with Bpoc amino acids, the resin-bound peptide aggregation caused by an asparagine residue was so extreme that stepwise coupling was impossible and the synthesis and coupling of di- and tripeptides was necessary to obtain suitable yields (8, 11).

A side-chain protecting group for Bpoc derivatives of asparagine or glutamine preferred for use in synthesis employing phenyl ester-, or allyl ester-type resins, or the like, should eliminate the dehydration side reaction that is characteristic of couplings done with unprotected asparagine residues, should disrupt rather than promote aggregation of resin-bound peptides and should be removable under the same deprotection conditions (TFA scavenger mixtures) as are used for the removal of tert-butyl groups. In addition, any carbocation produced during deprotection should not alkylate tryptophan residues. Preferred side-chain protected Bpoc amino acids should exhibit high solubility in $CH_2Cl_2$ or dichloroethane, or other suitable solvent for solid-phase synthesis and should be obtainable as a crystalline solid. The trityl group (Trt, see: Sieber and Riniker, 40) is a side-chain blocking group for asparagine and glutamine, i.e., a carboxamide protecting group, which was found to satisfy the requirements listed above.

The primary function of the side-chain protecting group of asparagine or glutamine is to enhance the solubility and reduce side reactions during coupling. It is not mandatory that the side-chain protecting group remain attached to the carboxamide of the growing peptide for the duration of a solid-phase synthesis, although this property is desirable in terms of reducing resin-bound peptide aggregation. HPLC analysis of aliquots taken from solutions of Fmoc-Gln (Trt)—OH and Fmoc-Asn(Trt)—OH in 0.5% TFA in $CH_2Cl_2$ indicates that the trityl group is cleaved less than 0.1% during the repetitive steps of a $N^\alpha$-Bpoc-based solid-phase peptide synthesis. For deprotection of the trityl group at the end of the synthesis, prior studies (40) have shown that the complete removal the trityl group from Asn and Gln side-chains can be accomplished in less than 1 h by treatment with 95% TFA scavenger mixtures.

Other appropriate, but less preferred, side-chain protecting groups for asparagine and glutamine include: 9-xanthenyl (Xan, 41); 2,4,6-trimethoxybenzyl (Tmob, 42); 4,4'-dimethylbenzhydryl (Mbh, 43); and 2,2', 4,4'-tetramethoxybenzhydryl (Tbh, 44).

Synthesis of certain side-chain protected Bpoc compounds (Bpoc-Asn(Trt)—OH and Bpoc-Gln(Trt)—OH is illustrated in Equation 1.

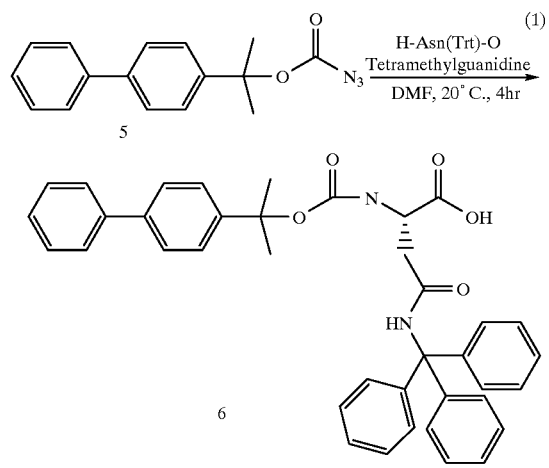

Bpoc-azid, formula 5, was prepared from acetylbiphenyl according to the procedure of Sieber and Iselin (1) as modified by Kemp et al. (28). Protected carboxamides H-Asn(Trt)—OH and H-Gln(Trt)—OH were prepared by the method of Sieber and Riniker (40). Treatment of the protected carboxamide with Bpoc-azide in DMF with tetramethylguanidine yielded the protected free amino acids Bpoc-Asn(Trt)—OH and Bpoc-Gln(Trt)—OH, formula 6, reproducibly in greater than 80% yield. In these preparations, both of the free acids were isolated as homogeneous, crystalline solids. It was not necessary to prepare cyclohexylamine or dicyclohexylamine salts in order to obtain crystalline solids as is often the case with Bpoc amino acids. The pentafluorophenyl esters of the protected free acids were prepared and found to be crystalline solids also. These Bpoc-amino acid pentafluorophenyl esters have shelf lives of at least one year when stored in the dark at –20° C. in a desiccated container. Bpoc-amino acids, when stored as the free acid under similar conditions, have shelf-lives that are usually less than a year before needing to be recrystallized. In terms of storage the active ester is preferable to a cyclohexylamine or dicyclohexylamine salt because it reduces the manipulations that are necessary when the Bpoc-derivative is removed from the freezer for use in peptide synthesis.

In addition to tBu, Trt, tBu-thio, Pmc, TFa, and allyl side group-protecting group that are specifically exemplified in the examples herein, Dnp (dinitrophenyl), Mtr (methoxytrimethylbenzenesulfonyl, Adoc (adamantyloxycarbonyl), Tmse (trimethylsilylethyl) groups can be employed as is known in the art amino acid side group protecting groups. The choice of a particular protecting group depends, as is well understood in the art, upon the amino acid side group to be protected and upon the conditions (deprotection conditions, coupling conditions, etc.) that are to be used in a given polypeptide synthesis.

The peptides, Acetyl-Ala-Phe-Asn(Trt)-Gly-Leu-Ala-O-Dbf-SH, formula 7 and Boc-Cys(Acm)-Ala-Phe-Gln(Trt)-Gly-Leu-Ala-O-Dbf-SH, formula 8, were prepared by stepwise solid phase peptide synthesis starting from the peptide resin of formula 4.

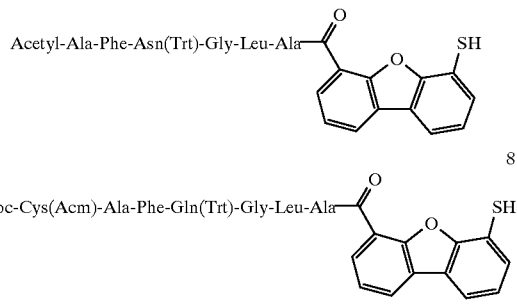

In solid phase polypeptide synthesis, an insoluble solid support or matrix, advantageously in bead form, is used. Such solid supports can be any of the solid phase polymeric substrates conventionally employed for the synthesis of polypeptides. Typical of such polymeric resins are crosslinked polystyrene resins, glass beads, clays, Celite, crosslinked dextran, polyacrylamides, polyamide resins, polyethylene glycol grafted polystyrene, and similar insoluble solid supports which either naturally contain reactive sites for coupling with the amino acid components or which can be provided with such reactive sites.

If desired, the solid phase polypeptide synthesis of the invention can be carried out in a flow reactor under pressure as described in U.S. Pat. No. 4,192,798, incorporated by reference in its entirety herein, but the use of supratmospheric pressures is not essential.

Several preliminary operations are necessary before the solid phase synthesis of a peptide can be started. First the supporting resin containing the C-terminal amino acid component of the proposed peptide chain must be prepared. This can be accomplished by any of a number of procedures known to one skilled in the art. Many of these solid supports, derivatized with N-protected amino acids, are articles of commerce and may be purchased as desired. Many of the common resin linkages (for the preparation of C-terminal peptide amides, peptide acids, and the like) can be prepared with Bpoc-amino acids as easily as with the other N-protected amino acids, and this may be accomplished by any of a number of procedures known to be skilled in the art.

The remaining synthesis to form the desired polypeptide sequence is carried out in the following manner. Before coupling of the second amino acid can take place, the first residue already on the support must be deprotected. Deprotection of the first amino acid residue on the resin as well as of each of the subsequently coupled amino acid residues can be carried out by contacting the protected amino acid residue with an appropriate deprotecting agent. The deprotecting agents employed for this purpose are well known to those of ordinary skill in the art of peptide synthesis and the particular deprotecting agent employed in any given instance will depend, of course, upon the deprotecting group on the amino acid/resin. For example, if the protecting group is t-butyloxycarbonyl, trifluoroacetic acid (usually 50% or higher) in dichloromethane or hydrochloric acid in a suitable solvent such as dioxane may be used. On the other hand, if the protecting group is 9-fluorenylmethyloxycarbonyl, basic conditions such as piperidine (usually 20%) in DMF will be the preferred method. If the protecting group for the first amino acid attached to the resin is Bpoc, like the Bpoc-amino acid Pfp or ODhbt esters of this invention, the deprotecting agent of choice will be 0.5% TFA in dichloromethane. Although it should be noted that one of the advantages of using the Bpoc-amino acid Pfp or ODhbt esters of this invention with some of the solid supports, such as polyethylene glycol grafted polystyrene, that swell in polar protic solvents, is the ability to deprotect the Bpoc group in dilute solutions (less than about 5% by volume) of trifluoroacetic acid in a solvent other (e.g., more polar) than dichloromethane, or to use solutions of glacial acetic acid in trifluoroethanol, ethanol and avoid using halogenated solvents and halogenated acids altogether. However, solutions of glacial acetic acid in dichloromethane can also be employed. The use of more polar solvents than dichloromethane in solid phase peptide synthesis will be recognized as an advantageous condition by those skilled in the art, since the use of more polar solvents disfavor resin-bound peptide aggregation phenomena following acidolytic removal of the Bpoc group. Glacial acetic acid is preferred in solid phase resin-based syntheses because it swells the resin.

After the deprotecting step, the resin is washed with a suitable solvent in order to remove excess deprotecting agents. If the deprotecting agent is a dilute solution of acid, such as the 0.5% TFA used to remove a Bpoc group, the subsequent step of neutralization with an appropriate non-nucleophilic tertiary amine base is greatly facilitated due to the very low concentration of acid to be neutralized relative to the same procedure after protection of the Boc group with high concentrations of trifluoroacetic acid, where the heat of neutralization becomes a serious problem in large scale solid phase polypeptide synthesis. Any excess tertiary amine or tertiary ammonium trifluoroacetate salt can be removed with a suitable solvent such as dichloromethane, dimethylformamide, or with solids supports with suitable swelling properties, ethanol or methanol. The resin-bound free amine, thus prepared, is now ready for coupling with the next N-protected amino acid.

If the next N-protected amino acid is a Bpoc-amino acid Pfp or ODhbt ester of the invention, it need not be activated and can be reacted directly in the presence of a non-nucleophilic tertiary amine base with the support now containing an unprotected resin bound amino acid. If, however, the N-protected amino acid component is to be coupled by more conventional procedures, it will be necessary to first activate, that is, convert it into a reactive form by any of a number of accepted procedures known to those of ordinary skill in the art of peptide synthesis. In general, an excess of the activated N-protected amino acid component is employed in the reaction. Concentration of the activated N-protected amino acid component is usually 0.1 M or greater.

After the coupling of the second protected amino acid component to the first amino acid component, the attached protected dipeptide is then deprotected, neutralized if necessary, and washed as described above before coupling of the next amino acid derivative is effected. This procedure is repeated until the desired sequence of amino acids has been assembled on the insoluble support. The completed peptide can be removed from the insoluble support by any of the standard methods as, for instance, by cleavage with trifluoroacetic acid (for appropriately functionalized alkoxybenzyl alcohol, alkoxybenzyl amine, or alkoxybenzhydrylamine resins), $Pd^0$/tributyltin hydride mixtures in dichloromethane (for appropriately functionalized allyl-type linkers), aminolysis, alcoholysis, or hydrolysis (for appropriately functionalized of the phenyl ester or oxime type).

After cleavage from the solid support, the resulting peptide is found to be remarkably homogenous and to require no or minimal purification. Because of the very low contamination of byproducts overall yields are found to be surprisingly high and whatever purification is necessary can be carried out with relative ease. Such purifications are preferably carried out by partition chromatography, ion exchange chromatography, reversed-phase high performance liquid chromatography or a combination of both. Such procedures are well-known to one skilled in the art of peptide synthesis.

The following examples illustrate the invention and are not intended to limit the scope of the invention.

EXAMPLES

Methods and Materials

Amino acids were purchased from Peptides International, Louisville, Ky. All amino acid derivatives were purchased from Advanced Chemtech (U.S.A.) and used without further purification. $N^\alpha$-Bpoc amino acids were prepared as described herein below or according to Kemp et al.(28). All other chemicals were purchased from Aldrich. ESI Mass Spectra were obtained on a Sciex API 1 instrument. Routine $^1$H NMR spectra were obtained on Brucker AM-250 FT (250 MHz) or AM-300 FT (360 MHz) spectrometers (Aspect 2000 computer, 32K memory space). $^{13}$C NMR Spectra were obtained on the same instruments (62.9 and 90.55 MHz). Chemical shifts are recorded in ppm downfield from tetramethylsilane. Analytical HPLC was performed on a Vydac 218TP54 reversed-phase, C-18 column and preparative HPLC was performed on a Vydac 218TP1022 reversed-phase C-18 column. All gradients reported are linear from Eluent A (0.1% TFA aq.) and Eluent B (0.1% TFA in 90% MeCN aq.).

Abbreviations used for amino acids and the designations of peptides follow the rules of the IUPAC-IUB Commission of Biochemical Nomenclature, see: *J. Biol. Chem.* (1972) 247, 977–983. Other abbreviations used are those generally known to those in the art including: Acm (acetamidomethyl); Alloc (the alkyl urethane, allyloxycarbonyl) EtOAc (ethyl acetate); Boc (tert.-butyloxycarbonyl); tBu (tert.-butyl); DCC (N,N'-dicyclohexylcarbodiimide); DCU (N, N'-dicyclohexylurea); DIC (diisopropylcarbodiimide); DIEA (N,N-diisopropylethylamine); DMF (N,N-dimethylformamide); Fmoc (9-fluorenylmethyloxycarbonyl); TFA (trifluoroacetic acid); TFMSA (trifluormethanesulfonic acid); Tfa (trifluoroacetate); Trt (trityl); Pmc (pentamethylchroman); MBHA (4-methylbenzhydrylamine resin); MeCN (acetonitrile); as well as other abbreviations identified, for example, in Barany et al. (47).

Example I

General Procedure for the Synthesis of Bpoc-Xxx-Pfp, where Xxx=Ala, Val, Ile, Leu, Pro, Met, Lys(Boc), Lys (Alloc), Phe, Lys(Tfa)

The free acid, Bpoc-Xxx-OH, was prepared according to the procedure of Kemp et al. (28) with the following modifications. The amino acid zwitterion (20 mmol) was solubilized in Triton B (22 mmol of a 40% solution in MeOH) and then concentrated on a high vacuum rotary evaporator to remove any excess $H_2O$ and $CH_3OH$. The white syrupy solid was mixed well with DMF (3–4 mL) and the suspension concentrated to a syrup on a high vacuum rotary evaporator. This step was repeated three times. The resulting heavy syrup was mixed with a minimum amount of DMF (5 mL) and Bpoc-O-Ph (20 mmol), and placed in a 55° C. silicon oil bath. After stirring for 3 h, the DMF was removed with the high vacuum rotovap. The pasty solid was diluted with $H_2O$ (20 mL), $Na_2SO_4$ (0.5 g, helps to prevent emulsions in some cases), and then overlayered with ether (20 mL). The layers were separated and the aqueous phase extracted twice more with ether. The combined ether washes were back extracted with 1% $NaHCO_3$ aq. and the aqueous phases combined, cooled in a 0° C. ice bath and overlayered with ether (40 mL). Dropwise addition of 0.5 M pH 3.5 citrate buffer to the biphasic mixture caused clouding in the aqueous layer that was cleared upon swirling. Addition was continued until pH 3.5 was reached in the mixture. The aqueous phase was extracted with ether (3×25 mL) and the ether combined and washed with citrate buffer (2×25 mL), water (2×25 mL), brine (1×25 mL), dried over $MgSO_4$, filtered and concentrated in vacuo to an oily solid (Yields: 60–95%). The Bpoc-Xxx-OH (20 mmol) prepared above was dissolved in THF (5 mL) and cooled to −10° C. in an acetone ice bath. Pentafluorophenol (19.5 mmol) and DCC (19.5 mmol) were added sequentially in one portion and the reaction allowed to stir for 2 h. The reaction was then filtered to remove DCU, the EtOAc removed in vacuo, and the reaction taken up in ether (10 mL) and allowed to sit overnight in a −20° C. freezer. Residual DCU was removed by filtration and the ether was removed in vacuo to an oil that either crystallized in isopropanol/hexanes or remained as an oil.

Example II

General Procedure for the Synthesis of Bpoc-Xxx-Pfp, where Xxx=Trp, Ser(tBu), Thr(tBu), Glu(tBu), Asp(tBu), Asn(Trt), Gln(Trt), His(Trt), Arg(Pmc), Tyr(Allyl) and Cys (tBu-thio)

To a solution of the amino acid zwitterion (20 mmol) and Bpoc-azide (20 mmol) in DMF (10 mL) was added tetramethylguanidine (40 mmol). After stirring under $N_2$ for 4 h, the reaction was poured into cold 1% $NaHCO_3$ (40 mL) and extracted with ether (3×20 mL). The combined ether layers were back-extracted with 1% $NaHCO_3$ (1×10 ml). The combined aqueous layers were cooled to 4° C. in an ice bath, overlayered with EtOEt (25 mL), and acidified to pH 3.5 by addition of 0.5 M pH 3.5 citrate buffer (if solubility difficulties are encountered, use EtOAc rather than EtOEt). The acidic aqueous layer was extracted twice more with EtOEt (25 mL), and the EtOEt layers were combined and washed with water (2×), brine (1×), dried over $MgSO_4$, and concentrated in vacuo. The Bpoc-Xxx-OH (15 mmol) prepared above was dissolved in THF or EtOAc (5 mL) and cooled to −10° C. in an acetone ice bath. Pentafluorophenol (14.8 mmol) and DCC (14.8 mmol) were added sequentially in one portion and the reaction allowed to stir for 2 h. The reaction was then filtered to remove DCU and the solvent removed in vacuo. Further details specific for each derivative are listed individually below.

Example III

Bpoc-Gly-Pfp

Bpoc-Gly-OH was prepared according to the procedure of Kemp et al. (28) with the following modification. A suspension of glycine (1.36 g, 18 mmol) and Triton B (19 mmol, 9 mL of a 40% solution in MeOH) was concentrated on the high vacuum rotary evaporator to remove any excess $H_2O$ and $CH_3OH$. The white syrupy solid was mixed well with DMF (3–4 mL) and the suspension concentrated to a syrup on a high vacuum rotary evaporator. This step was repeated three times. The resulting heavy suspension was mixed with a minimum amount of DMF (5 mL) and Bpoc-O-Ph (4 g, 12 mmol), and placed in a 55° C. silicon oil bath. After stirring for 3 h, the DMF was removed with the high vacuum rotovap. The pasty solid was diluted with $H_2O$ (20 mL), and then overlayered with ether (20 mL), cooled in an ice bath and acidified with pH 3.5 citric acid buffer. Immediately upon acidification a white solid precipitated and was collected by filtration, washed with H$_2$O and ether, and dried under vacuum to afford Bpoc-Gly-OH as a white powder (3.56 g, 95%). mp=129° C. (lit 131–132° C.).[23] Bpoc-Gly-OH (3.56 g, 11.4 mmol) and pentafluorophenol (2.66 g, 14.5 mmol) were dissolved in a 1:1 CH$_2$Cl$_2$/EtOAc (15 mL) and cooled in a −10° C. bath. After 5 min DCC (3.0 g, 14.5 mmol) was added and the reaction allowed to stir at 0° C. for 2 h. DCU was removed by filtration and the reaction was allowed to sit at −20° C. overnight. Residual DCU was removed by filtration and the reaction was concentrated in vacuo to an oil that was taken up in 2-propanol/ hexanes and placed in the −20° C. freezer. After 12 h, white crystals (3.8 g, 66%) were collected by filtration and washed with cold hexanes. mp 117° C. HPLC: t$_R$=7.2 min. (25% B to 75% B over 30 min.).

Example IV
Bpoc-Ala-Pfp

The residue obtained from the general procedure of Example I given above was esterified in EtOAc and the Pfp ester was crystallized from 2-propanol/hexanes to yield a white solid (73%). mp 96–99° C. $[\alpha]^{21}_{589}$=−47.0. HPLC (75% B to 100% B over 20 min): t$_R$=9.2 min.

Example V
Bpoc-Val-Pfp

The residue obtained from the general procedure of Example I was crystallized from neat hexanes and was obtained as white crystals. mp. 52–58° C. $[\alpha]^{21}_{589}$=−33.9. HPLC (75% B to 100% B over 20 min): t$_R$=12.3 min.

Example VI
Bpoc-Leu-Pfp

The residue obtained from the general procedure of Example I was esterified in EtOAc and the Pfp ester was crystallized from EtOAc/hexanes to yield a white solid (72%). mp 95–97° C. $[\alpha]^{21}_{589}$=−35.7. HPLC (75% B to 100% B over 20 min): t$_R$=13.8 min.

Example VII
Bpoc-Ile-Pfp

The residue obtained from the general procedure of Example I was esterified in EtOAc and the Pfp ester was crystallized from isopropanol/hexanes to yield a white solid (19%). mp.76–79° C. $[\alpha]^{21}_{589}$=−35.4. HPLC (75% B to 100% B over 20 min): t$_R$=14.1 min.

Example VIII
Bpoc-Pro-Pfp

The residue obtained from the general procedure of Example I was esterified in EtOAc and crystallized from isopropanol/hexanes to yield a white solid (35%). mp 97–100° C. $[\alpha]^{21}_{589}$=−36.3. HPLC (75% B to 100% B over 20 min): t$_R$=12.3 min.

Example IX
Bpoc-Met-Pfp

The residue obtained from the general procedure of Example I was esterified in EtOAc and crystallized from isopropanol/hexanes to yield a white solid (21%). mp 68–72° C. $[\alpha]^{21}_{589}$=−31.0. HPLC (75% B to 100% B over 20 min) t$_R$=10.8 min.

Example X
Bpoc-Phe-Pfp

The residue obtained from the general procedure of Example I was esterified in EtOAc and crystallized from EtOAc/hexanes to yield a white solid(65%). mp 123–125° C. $[\alpha]^{21}_{589}$=−34.4. HPLC (75% B to 100% B over 20 min): t$_R$=12.5 min.

Example XI
Bpoc-Tyr(Allyl)-Pfp

The residue obtained from the general procedure of Example II was esterified in EtOAc and crystallized from isopropanol/hexanes to yield a white solid (40%). mp 135–136° C. $[\alpha]^{21}_{589}$=−18.1. HPLC (75% B to 100% B over 20 min): t$_R$=14.5 min.

Example XII
Bpoc-Trp-Pfp

The residue obtained from the general procedure of Example II was solidified upon addition of ether to yield a foam (61%). After two recrystallizations from isopropanol/hexanes, colorless crystals, mp 50–52° C., are obtained. $[\alpha]^{21}_{589}$=−18.9. HPLC(75% B to 100% B over 20 min): t$_R$=11.24 min.

Example XIII
Bpoc-Glu(tBu)-Pfp

The residue obtained from the general procedure of Example II was obtained as an amorphous solid at room temperature. $[\alpha]^{21}_{589}$=−21.6 HPLC (75% B to 100% B over 20 min): t$_R$=14.0 min.

EXAMPLE XIV
Bpoc-Asp(tBu)-Pfp

The residue obtained from the general procedure of Example II was crystallized from neat hexanes containing only a few drops of ether. Yield 95%. mp 81–85° C. $[\alpha]^{21}_{589}$=−25.5. HPLC (75% B to 100% B over 20 min): t$_R$=13.9 min.

Example XV
Bpoc-Asn(Trt)-Pfp

Bpoc-Asn(Trt)—OH: H-Asn(Trt)—OH was prepared according to the procedure of Sieber and Riniker (40) with the following modifications. H-Asn-OH (13.2 g, 0.1 mol), trityl alcohol (52 g, 0.2 mol), conc. H$_2$SO$_4$ (6.1 mL, 0.115 mol) were suspended in glacial acetic acid (300 mL) for 10 min. Acetic anhydride (9 mL, 0.2 mol) was added and the reaction was heated to 60° C. After 4 h the solution was slowly added to cold water (600 mL) and adjusted to pH 6 by addition of 10 N NaOH. After 1 h at 0° C., white crystals were collected and washed thoroughly with water and toluene. Drying under vacuum for 24 h yielded white crystals (36 g, 94%). mp>240 dec., lit. >240 dec.

To a solution of H-Asn(Trt)—OH (600 mg, 1.6 mmol) and Bpoc-azide (674 mg, 2.47 mmol) in DMF (10 mL) was added tetramethylguanidine (0.4 mg, 3.2 mmol). After stirring under N$_2$ for 4 h, the reaction was poured into cold saturated NaHCO$_3$ and extracted with ether (2×20 mL). The aqueous layer was cooled to 4° C. by addition of ice, overlayered with EtOAc (25 mL), and acidified to pH 3.5 by addition of 1 M citric acid solution. The acidic aqueous layer was extracted twice more with EtOAc, and the EtOAc layers were combined and washed with water (2×), brine (1×), dried over MgSO$_4$, and concentrated in vacuo to a lumpy solid having a slight yellow tint. Trituration with ether (2×15 mL) yielded a white powder (700 mg, 71%). mp 134–135° C. HPLC (60% B to 100% B in 20 min): t$_R$=14.2 min (100%).

Bpoc-Asn(Trt)-Pfp

To a solution of Bpoc-Asn(Trt)—OH (2.1 g, 3.4 mmol) and pentafluorophenol (0.66 g, 3.6 mmol) in EtOAc (15 mL)

at 0° C. was added DCC (0.73 g, 3.6 mmol) and the reaction stirred for 3 h. The DCU was removed by filtration and the filtrate concentrated in vacuo to a white solid that was recrystallized from isopropanol/hexanes to yield white needles (2.5 g, 95%) mp=128–130° C. HPLC (75% B to 100% B over 20 min): $t_R$=14.8 min (100%).

Example XVI

Bpoc-Gln(Trt)-Pfp

Bpoc-Gln(Trt)—OH: H-Gln(Trt)—OH was prepared according to the procedure of Sieber and Riniker (40) without modification. To a suspension of H-Gln(Trt)—OH (620 mg, 1.6 mmol) in DMF (10 mL) was added tetramethylguanidine (0.4 mL, 3.2 mmol) and within 2 min everything had dissolved. To this solution was added Bpoc-azide (674 mg, 2.47 mmol). After stirring under $N_2$ for 4 h, the reaction was poured into cold saturated $NaHCO_3$ and extracted with ether (2×, 20 mL). The aqueous layer was cooled to 4° C. by addition of ice, overlayered with EtOAc (25 mL), and acidified to pH 3.5 by addition of 1 M citric acid solution. The acidic aqueous layer was extracted twice more with EtOAc, and the EtOAc layers were combined and washed with water (2×), brine (1×), dried over $MgSO_4$, and concentrated in vacuo to a lumpy solid having a slight yellow tint. Trituration with ether (2×, 15 mL) yielded a white powder (900 mg, 90%). mp 102–104° C. HPLC (60% B to 100% B in 20 min): $t_R$=14.8 min (100%).

Bpoc-Gln(Trt)-Pfp

To a solution of Bpoc-Gln(Trt)—OH (2.5 g, 4.0 mmol) and pentafluorophenol (0.77 g, 4.2 mmol) in EtOAc (15 mL) at 0° C. was added DCC (0.86 g, 4.2 mmol) and the reaction stirred for 3 h. The DCU was removed by filtration and the filtrate concentrated in vacuo to a white solid that was recrystallized from isopropanol/hexanes to yield white needles (3.04 g, 96%), mp 148–150. HPLC (75% B to 100% B over 20 min): $t_R$=15.9 min (100%).

Example XVII

Bpoc-Arg(Pmc)-Pfp

The procedure of Example II was followed. Esterification done in THF at −40° C. over 4 h. After removal of DCU, the solvent was removed in vacuo and the oily residue solidified as quickly as possible by addition of 1/1 ether hexanes. Isolation and characterization of Bpoc-Arg(Pmc)-Pfp is complicated due to concomitant formation of the d-lactam during crystallization and during analysis by NMR. Initially, $^1$H NMR resonances are broad, with Pfp ester resonances diminishing and D-lactam resonances growing with time. After 12 h in $CDCl_3$, resonances are sharp peaks corresponding to exclusively to the D-lactam. The best results were obtained by the rapid precipitation described above. Recrystallization was usually counterproductive, as D-lactam formation was always faster than crystallization.

Example XVIII

Bpoc-Ser(tBu)-Pfp

The residue obtained from the general procedure of Example II was esterified in EtOAc 0° C. for 6 h. The Pfp ester was freely soluble in neat hexanes and was obtained as a pure and colorless oil (85%). HPLC (75% B to 100% B over 20 min): $t_R$=15.4 min (100%).

Example XIX

Bpoc-Thr(tBu)-Opfp

The residue obtained from the general procedure of Example II was crystallized from hexanes containing a few drops of ether yielding a white solid. mp 68–72° C. $[\alpha]^{25}_{589}$=−39.6. HPLC (60% B to 100% B over 20 min): $t_R$=16.9 min.

Example XX

Bpoc-Lys(Tfa)-Pfp

The residue obtained from the general procedure of Example II was crystallized from hexanes containing a few drops of ether, yielding a white solid. mp 139–140° C. $[\alpha]^{25}_{589}$=−30.8. HPLC (75% B to 100% B over 20 min): $t_R$=10.0 min.

Example XXI

Bpoc-His(Trt)—OH

Bpoc-His(Trt)—OH obtained from the general procedure of Example II was obtained as a crystalline solid (91%). mp=104–105° C. $[\alpha]^{21}_{589}$=36.7. HPLC (60% B to 100% B over 20 min): $t_R$=8.85 min (100 %).

Example XXII

Bpoc-His(Trt)-Pfp

To a solution of Bpoc-His-(Trt)—OH (2.1 g, 3.14 mmol) in EtOAc (20 ml) at −10° C., pentafluorophenol (0.578 g, 3.14 mmol, 1 equiv ) and DCC (0.641 g, 3.14 mmol, 1 equiv) were added. After 10 h at −10° C., the precipitate was filtered and the filtrate was concentrated at high vacuum. A brown foam was obtained when the filtrate was concentrated at high vacuum. The crude product was dissolved in 1:1 ethyl ether and hexanes solution (40 ml) at RT, and the impurity was removed by filtration. A white crystalline solid (1.8 g, 2.4 mmol, 75%) was precipitated when the solution was concentrated to one fourth of its volume at 0° C. mp 82–84° C. $[\alpha]^{21}_{589}$=−26.6. HPLC (75% B to 100% B over 20 min): $t_R$=8.7 min.

Example XXIII

Bpoc-Cys (tButhio)-Pfp

The residue obtained from the general procedure given above was crystallized from neat hexanes containing only a few drops of ether. Yield 92%. mp 104–107° C. $[\alpha]^{21}_{589}$=−67.4. HPLC (75% B to 100% B over 20 min): $t_R$=12.20 min (97%).

Example XXIV

Bpoc-Arg(Pmc)-Pfp

The procedure of Example II was used. Esterification was done in THF at −40° C. over 2 h. After removal of DCU, the solvent was removed in vacuo and the oily residue solidified as quickly as possible by addition of 1/1 ether hexanes. Isolation and characterization of Bpoc-Arg(Pmc)-Pfp is complicated due to concomitant formation of the d-lactam during crystallization and during analysis by NMR. The best results were obtained by the rapid precipitation described in Example XVII. Recrystallization was usually counterproductive, as d-lactam formation was always faster than crystallization.

Example XXV

Bpoc-Phe-Ala-OMe

Bpoc-Phe-Pfp (100 mg, 0.176 mmol) and H-Ala-OMe: HCl (55 mg, 0.39 mmol) were dissolved in DMF (2 mL). DIEA (92 mL, 0.528 mmol) was added and the reaction stirred at RT for 2 h. The reaction mixture was poured into EtOAc (40 mL) and extracted with 0.5 M citric acid buffer pH 3.5 (3×15 mL), 5% aq. $NaHCO_3$ (3×15 mL), water (3×15 mL), and brine (2×15 mL). The organic phase was dried over $MgSO_4$, filtered, and concentrated in vacuo to give an oil that was placed under 0.1 torr vacuum for 3 h. Yield 93%. HPLC (75% B to 100% B over 20 min): $t_R$=12.2 min.

Example XXVI
Bpoc-Phe-Gly-OMe

Prepared according to the same procedure used for Bpoc-Phe-Ala-OMe. Yield 97%. $[\alpha]^{21}_{589}=-5.3$. HPLC (75% B to 100% B over 20 min): $t_R=11.2$ min.

Example XXVII
Bpoc-Pro-Ala-OMe

Prepared according to the same procedure used for Bpoc-Phe-Ala-OMe. Yield 99%. $[\alpha]^{21}_{589}=-19.8°$. HPLC (75% B to 100% B over 20 min): $t_R=8.5$ min.

Example XXVIII
Bpoc-Pro-Gly-OMe

Prepared according to the same procedure used for Bpoc-Phe-Ala-OMe. Yield 81%. HPLC (75% B to 100% B over 20 min): $t_R=7.2$ min.

Example XXIX
Solid-Phase Peptide Synthesis of the test peptide H-Lys-Val-Val-Val-Val-Val-NH$_2$ Starting with an MBHA resin loaded with Valine (0.57 mmol/g, 100 mg), four cycles of (i) coupling with 0.1 M Bpoc-Val-Pfp (0.228 mmol), DIEA (0.456 mmol), 1 equiv. HOBt (0.228 mmol), in 1:1 CH$_2$Cl$_2$/DMF, 2 h (ii) deprotection of the Bpoc group with 0.5% TFA in CH$_2$Cl$_2$, 1×3 min, 1×15 min., (iii) wash with CH$_2$Cl$_2$, 4×8 mL, (iv) wash with 5% DIEA in CH$_2$Cl$_2$, (v) wash with CH$_2$Cl$_2$, 2×8 mL were performed. After the four Bpoc cycles, Fmoc-Lys(Boc)—OH was coupled onto the amine terminus with DIC/HOBt. After removal of the Fmoc group with 20% piperidine in DMF and removal of the Boc group in 95% TFA in CH$_2$Cl$_2$, the peptide was released from the resin with a solution of TFA containing 1 M TFMSA and 1 M thioanisole, 0° C., 4 h. Trituration with ether yielded an off white powder (27 mg, 67%) that was eluted through a Vydac preparative C18 HPLC column and lyophilized to a white flocculent solid. HPLC: $t_R=18.0$ min (10% B to 70% B in 20 min). ESI MS: 642 MH$^+$.

Example XXX
Solid-Phase Peptide Synthesis of Substance P, H-Arg-Pro-Lys-Pro-Gln-Gln-Phe-Phe-Gly-Leu-Met-NH$_2$ Starting with an MBHA resin loaded with methionine (0.57 mmol/g, 100 mg), ten cycles of (i) coupling with 0.1 M Bpoc-Xxx-Pfp (0.228 mmol), DIEA (0.456 mmol), HOBt (0.114 mmol), in DMF, 2 h (ii) deprotection of the Bpoc group with 0.5% TFA in CH$_2$Cl$_2$, 1×3 min, 1×15 min., (iii) wash with CH$_2$Cl$_2$, 4×8 mL, (iv) wash with DMF, 2×8 mL were performed. Side-chain protection used was Gln(Trt), Lys(Tfa), Arg(Pmc). At the completion of the synthesis, the Trt and Pmc groups were removed with 95% TFA/1% H$_2$0/4% ethanedithiol, 30 min. The deprotected, resin-bound peptide (70 mg weight gain on resin) was cleaved from the resin with 1 M TFMSA/1 M thioanisole in TFA (4° C., 4 h), precipitated with ether and triturated with ether (6×) to yield an off-white flocculent powder (61 mg, 69%). This residue was placed in 0.1 M Ba(OH)$_2$ in 1:1 MeOH/H$_2$O 2h, and eluted through a C18 Vydac preparative HPLC column HPLC (10% to 70% B in 30 min): Substance P, $t_R$=min. HPLC (10% to 70% B in 30 min): Substance P(Tfa), tR=min. ESI mass spectrum, Substance P: 1347 MH+, -Met-NH$_2$, MH$^+$-Leu-Met-NH$_2$. ESI mass spectrum, Substance P (Tfa): 1443.6, MH$^+$; 1295.6, MH$^+$-Met-NH$_2$; 1182.6, MH$^+$-Leu-Met-NH$_2$; 1125.6, MH$^+$-Gly-Leu-Met-NH$_2$.

Example XXXI
Solid-Phase Synthesis of Acetyl-Ala-Phe-Asn(Trt)-Gly-Leu-Ala-O-Dbf-SH, Formula 7 and Boc-Cys(Acm)-Ala-Phe-Gln(Trt)-Gly-Leu-Ala-O-Dbf-SH, Formula 8

Each of these peptides was prepared on the thiol capture resin, 4, by standard solid-phase peptide synthesis methods using preformed N$^\alpha$-Bpoc trityl-protected pentafluorophenyl esters of asparagine and/or glutamine and N$^\alpha$-Bpoc-amino acid preformed symmetrical anhydrides (Bpoc-NH-CHR-CO)$_2$—O of the other amino acids (9). The peptide was cleaved from the resin using an excess of tributylphosphine in an 8:1 CH$_2$Cl$_2$/HFIP mixture and then triturated with ether and purified by HPLC on a Vydac C18 column. HPLC of 7 (Eluent 60% B to 100% B over 20 min.): $t_R$=14.0 min, 100%. ESI MS of 7 (Infusion injection, CH$_3$CN, H$_2$O, 1% acetic acid): 1074 (M+). HPLC of 8 (Eluent 60% B to 100% B over 20 min.): $t_R$=15.9 min, 100%. ESI MS of 8 (Infusion injection, CH$_3$CN, H$_2$O, 1% acetic acid): 1320 (M+).

In couplings of the Bpoc-Asn(Trt) and Bpoc-Gln(Trt), a concentration of 0.2 M in neat CH$_2$Cl$_2$ was achieved for both the preformed symmetrical anhydride and the Pfp ester. It was not necessary to add any DMF for solubility purposes, thus minimizing the possibility of phenyl ester cleavage reactions that are enhanced in a dipolar aprotic solvent such as DMF. It is useful to note that with the trityl group attached, peptides of formula 7 and 8 are highly soluble in CH$_3$CN, CH$_3$OH, and DMF. When the trityl group is removed from either 7 or 8, the solubility is of the deprotected peptide greatly diminished.

Example XXXII
Removal of the N-Lys(Tfa) side chain protecting group

To the resin-bound tetrapeptide H-Leu-Leu-Phe-Phe-MBHA, which was assembled in the same manner described for the peptides above starting with MBHA resin (0.57 mmol/g, ca. 100 mg), was added Bpoc-Lys(Tfa)-Pfp (0.228 mmol), DIEA (0.456 mmol), HOBt (0.114 mmol), in DMF (0.1 M). The coupling proceeded for 2 h, and the Bpoc group was removed as described above. The peptide was released from the resin with the TFMSA/thioanisole TFA mixture described above and precipitated and triturated with ether to yield a white flocculent solid that gave a single sharp peak by HPLC with the correct mass spectrum. No peptide containing a Tfa-protected lysine was observed. HPLC (250% to 75% B in 30 min): $t_R$=16.0 min ESI MS: 666, MH$^+$; 503, MH$^+$-PheNH$_2$.

Example XXXIII

The synthesis of compounds Bpoc-Xxx-ODhbt where Xxx includes Ala, Val, Ile, Leu, Pro, Met, Lys(Boc), Lys(Alloc), Phe, Lys(Tfa), Trp, Ser(tBu), Thr(tBu), Glu(tBu), Asp(tBu), Asn(Trt), Gln(Trt), His(Trt), Arg(Pmc), and Tyr(Allyl) and other compounds of Table 1.

The general synthesis of ODhbt esters is exemplified by the synthesis of Bpoc-Ala-ODhbt.

Bpoc-Ala-ODhbt

To a suspension of H-Ala-OH (1.34 g, 15 mmol) in DMF (5 mL) was added "TRITON B" (6.81 mL, 15 mmol) and with gentle swirling, everything had dissolved within 5 minutes. The resulting suspension was placed on the high vacuum rotary evaporator to remove any excess water and methanol. The syrupy solid was mixed well with a minimum amount of DMF (2–4 mL) and the solvent was removed in vacuo. This step was repeated 3×. The resulting heavy suspension was mixed with a minimum amount of DMF and Bpoc-O-Ph (3.00 g, 9.0 mmol) was added. After stirring under N$_2$ for 3 h at 55° C., the reaction was poured into cold NaHCO$_3$ (5.0%) and extracted with diethyl ether (3×, 20 mL). The ether extracts were back extracted with NaHCO$_3$ (5.0%). The combined aqueous layers were overlayered with ether and cooled in an ice bath for five minutes. Buffered citric acid (1.0 M) was added, upon which clouding occurred. Buffer was added until no more clouding was noticeable and pH 4 was achieved. The layers were then separated and the aqueous layer extracted twice more with ether. The pooled ether layers were washed successively with 1.0 M buffered citric acid 2x, water 3x, and brine 3x. The ether was then dried over $Na_2SO_4$ for 30 minutes. With a water aspirator rotary evaporator, the ether was removed and the resulting oil further dried with a high vacuum for 15 min. The viscous oil (2.41 g, 7.34 mmol) was taken up in THF (10 mL) and cooled to 0 in an ice bath for 10 min. DCC (0.95 eq, 1.44 g, 6.98 mmol) was dissolved in a minimum amount of THF and added to the dissolved oil. HODhbt was then added to the flask and the reaction mixture was allowed to stir at 0° for 6 h. The DCU was filtered with a Buchner funnel and the clear yellow oil was taken up in ether (20 mL) and left in the freezer overnight. The excess DCU and HODhBt were then filtered off and the solvent removed in vacuo. The product was crystallized from ether/hexanes to give a white solid (3.03 g, 87%). mp 111°–113° C. HPLC (60% B to 100% B in 20 min): $t_R$=14.2 min.

Example XXXIV
Bpoc-Ser(tBu)-ODhBt

Bpoc-Ser(tBu)—OH (0.370 g, 0.927 mmol), prepared according to the general procedure of Example XXXIII with Triton B and Bpoc-OPh, was taken up in a minimum amount of THF (1 mL) and cooled to –10° C. in an ice/acetone bath for 10 min. Pre-dissolved DCC ( 0.191 g, 0.927 mmol) was added to the solubilized oil. A solution of HODhBt (0.151 g, 0.881 mmol) was immediately added to the flask and the reaction mixture was allowed to stir at –15° C. for 2 h. The DCU was removed by filtration and the clear yellow oil was taken up in ether and left in the freezer overnight. The excess DCU and HODhBt was then filtered off and the solvent removed in vacuo. The product was crystallized from ether/ hexanes to give a white crystalline solid (0.300 g, 61%). mp 84–88° C. HPLC (60% B to 100% B in 20 min):$t_R$=16.59 min. $[\alpha]^{21}$ =–59.1°.

Other Bpoc-Xxx-ODhbt esters, including side-group protected esters can be prepared by methods described herein or by routine adaptation of those methods in view of methods and techniques well known to those in the art.

Those of ordinary skill in the art will appreciate that methods, techniques, procedures, syntheses, starting materials, side-chain protecting groups, reagents and reaction conditions other than those specifically described herein can be employed with expense of undue experimentation to achieve the objects of this invention. All such routine adaptation or modifications or functional equivalents of the specific embodiments and examples disclosed herein are considered to fall within the spirit and scope of this invention.

All references cited herein are incorporated in their entirety by reference herein.

TABLE 1

Summary of Properties of Bpoc-ODhbt Amino Acid Esters

| Compound | mp(° C.) | $[\alpha]_D^{20}$ [1] | HPLC [2] |
|---|---|---|---|
| Bpoc-Gly-ODhbt | 121–123 | — | 9.9 |
| Bpoc-Ala-ODhbt | 111–113 | –117 | 11.1 |
| Bpoc-Val-ODhbt | 116–120 | –122 | 14.1 |
| Bpoc-Leu-ODhbt | 78–80 | –93.6 | 15.7 |
| Bpoc-Ile-ODhbt | foam | –77.5 | 15.8 |
| Bpoc-Pro-ODhbt | 68–71 | –100 | 13.8 |

TABLE 1-continued

Summary of Properties of Bpoc-ODhbt Amino Acid Esters

| Compound | mp(° C.) | $[\alpha]_D^{20}$ [1] | HPLC [2] |
|---|---|---|---|
| Bpoc-Met-ODhbt | foam | –73.7 | 13.7 |
| Bpoc-Cys(tButhio)-ODhbt | | –113 | 12.6 |
| Bpoc-Phe-ODhbt | 74–80 | –64.6 | 15.4 |
| Bpoc-Tyr(allyl)-ODhbt | 98–102 | –45.6 | 16.9 |
| Bpoc-Trp-ODhbt | 138–139 | –67.1 | 14.1 |
| Bpoc-Ser(tBu)-ODhbt | 84–88 | –59.1 | 16. |
| Bpoc-Thr(tBu)-ODhbt | 110–111 | –47.7 | 18.5 |
| Bpoc-Asp(tBu)-ODhbt | 74–80 | –81.5 | 15.6 |
| Bpoc-Glu(tBu)-ODhbt | amorph. | –85.8 | 16.0 |
| Bpoc-Asn(Trt)-ODhbt | 122–123 | –45.5 | 18.8 |
| Bpoc-Gln(Trt)-ODhbt | 119–121 | –42.2 | 18.9 |
| Bpoc-His(Trt)-ODhbt | 112–118 | +21.6 | 9.8 |
| Bpoc-His(Bum)-ODhbt | foam | –14.6 | 8.4 |
| Bpoc-Lys(Tfa)-ODhbt | foam | –77.8 | 12.8 |

[1] All of the optical rotation values are reported for c = 1 in DMF. @ c = 0.5 in DMF.
[2] All HPLC values were obtained on a Vydac C18 HPLC column using an eluent 60% B to 100% B over twenty minutes. Eluent B = 0.1% TFA in 90% $CH_3CN$ containing 10% water. Eluent A = 0.1% TFA in water.

REFERENCES

1. Sieber, P.; Iselin, B. (1968) *Helv. Chim. Acta* 51, 614–622.
2. Kamber, B.; Riniker, B.; Sieber, P.; Rittel, W. (1976) *Helv. Chim. Acta* 59, 2830–2840.
3. Sieber, P.; Kamber, B.; Hartmann, A.; Joehl, A.; Riniker, B.; Rittel, W. (1977) *Helv. Chim. Acta* 60, 27–37.
4. Galpin, I. J.; Kenner, G. W.; Ohlsen, S. R.; Ramage, R.; Sheppard, R. C.; Tyson, R. G. (1979) *Tetrahedron* 35, 2785–2790.
5. Galpin, I. J.; Hancock, F. E.; Handa, B. K.; Jackson, A. G.; Kenner, G. W McDowell, P.; Noble, P.; Ramage, R. (1981) *Tetrahedron* 37, 3043–3050.
6. Mojsov, S; Merrifield, R. B. (1981) *Biochemistry* 20 2950–2957.
7. Kemp, D. S. (1981) *Biopolymers* 20, 1793–1804.
8. Kemp, D. S.; Carey, R. I.; Dewan, J.; Galakatos, N. G.; Kerkman, D.; Leung, S-L. (1989) *J. Org. Chem.* 54, 1589–1603.
9. Kemp, D. S.; Carey, R. I. (1993) *J. Org. Chem.* 58, 2216–2222.
10. Kemp, D. S.; Carey, R. I. (1991) *Tetrahedron Lett.* 32, 2845–2848.
11. Fotouhi, N.; Galakatos, N. G.; Kemp, D. S. (1989) *J. Org. Chem.* 54, 2803–2817.
12. Fotouhi, N.; Bowen, B.; Kemp, D. S. (1992) *Int. J. Peptide, Protein Res.* 40, 141–147.
13. Wang, S. S.; Yang, C. C.; Kulesha, I. D.; Sonnenberg, M.; Merrifield, R. B. (1974) *Int. J. Peptide Protein Res.* 6, 103–109.
14. Wang, S. S.; Merrifield, R. B. (1969) *J. Prot. Res.* 1 235–244.
15. Trudelle, Y.; Heitz, F. (1987) *Int. J. Peptide Protein Res.* 30, 163–169.
16. Colombo, R. (1981) *Bioorg. Chem.* 10, 219–232.
17. Galpin, I. J.; Kenner, G. W.; Ramage, R.; Thorpe, W. D. *Tetrahedron* 37, 3037–3041. See references therein, particularly for Peptides XXXIV to XXXXV for Bpoc-derivatives used in the synthesis of the Lysozyme analog.
18. Hiskey, R. G.; Wolters, E. T.; Ülkü, G.; Rao, V. R. (1972) *J. Org. Chem.* 37, 2478–2483.
19. Schwertner, E.; Berndt, H.; Gielen, H.-G.; Zahn, H. (1975) *Liebigs Ann. Chem.* 581–585.
20. Kovacs, J.; Mayers, G. L.; Johnson, R. H.; Cover, R. E.; Ghatak, U. R. (1970) *J. Chem. Soc. Chem. Comm.* 53–54.

21. Kovacs, J.; Mayers, G. L.; Johnson, R. H.; Cover, R. E.; Cover, R. E.; Ghatak, U. R. (1970) *J. Org. Chem.* 35, 1810–1812.
22. Kisfaludy, L.; Schön, I. (1983) *Synthesis,* 325.
23. Schön, I.; Kisfaludy, L. (1986) *Synthesis,* 303.
24. Atherton, E.; Carmeron, L. R.; Sheppard, R. C. (1988) *Tetrahedron* 44, 843–857.
25. Atherton, E.; Sheppard, R. C. (1985) *J. Chem. Soc. Chem. Comm.,* 165–166.
26. Hudson, D. (1990) *Peptide Res.* 3, 51–55.
27. Hudson, D. (1988) *J. Org. Chem.* 53, 617–624.
28. Kemp, D. S.; Fotouhi, N.; Boyd, J. G.; Carey, R. I.; Ashton, C.; Hoare, J. (1987) *Int. J. Peptide Protein Res.* 31, 359–372.
29. Feinberg, R. S.; Merrifield, R. B. (1972) *Tetrahedron* 28, 5865–5875.
30. Fotouhi, N.; Kemp, D. S. (1992) *Int. J. Peptide Protein Res.* 40, 153–161.
31. Rosowski, A.; Wright, J. E. (1989) *J. Org. Chem.* 54, 5551–5558.
32. Rosowski, A.; Wright, J. E. (1983) *J. Org. Chem.* 48, 1539–1541.
33. Carey, R. I., Huang, H.; Wadsworth, J. L.; Burrell, C. S. (1996) *Int. J. Peptide Prot. Res.* 47(3), 209–213.
34. Albericio, F.; Barany, G. (1987) *Int. J. Peptide Protein Res.* 30, 206–216.
35. Tam, J. P.; Merrifield, R. B. (1987) in *The Peptides: Analysis, Synthesis, Biology* (Undenfriend, S.; Meienhofer, J., eds.) Vol. 9, p. 236, Academic Press, New York.
36. Kunz, H.; Seitz, O. (1995) *Angew. Chem. Int. Ed. Engl.* 34, 803–805.
37. Kunz, H.; Dumbo, B. (1988) *Angew. Chem. Int. Ed. Engl.* 27, 711–713.
38. Guibe, F.; Dangles O.; Balavoine, G. (1989) *Tetrahedron Lett.* 30, 2641–2645.
39. Wang, S. S.; Kulesha, I. D. (1975) *J. Org. Chem.* 40, 1227–1234.
40. Sieber, P.; Riniker, B. (1991) *Tetrahedron Lett.* 32, 739–742.
41. Shimonishi, Y.; Sakakibara, S.; Adabori, S. (1962) *Bull. Chem.Soc. Japan* 35, 1966.
42. Weyand, F.; Steglich, W.; Bjarnason, J.; Akhtar, R.; Chytil, N. (1968) *Chem. Ber.* 101, 3623.
43. Koenig, W.; Geiger, R. (1970) *Chem. Ber.* 103, 2041.
44. Juhasz, A.; Bajusz, S. (1979) *Acta Chim. Acad. Sci. Hung.* 102, 289.
45. Hammond, G. S.; Reeder, C. E. (1958) *J. Am Chem. Soc.* 80, 572–575.
46. Atherton et al. (1988) *J. Chem. Soc. Perkins Trans.* I2887–2894.
47. Barany, G.; Kneib-Cordonier, N.; Muller, D. G. (1987) *Int. J. Peptide Protein Res.* 30, 705–739.

I claim:

1. A $N^{\alpha}$-2(p-biphenyl)-propyloxycarbonyl amino acid pentafluoro-phenyl ester which can be represented as Bpoc-Xxx-Pfp where Xxx is an amino acid, excluding those esters where the amino acid is L-glutamine, S-(acetamidomethyl)-L-cysteine, or L-(tert-butyl)-glutamic acid.

2. The compound of claim 1 wherein Xxx is selected from the group of amino acids consisting of glycine, alanine, valine, leucine, isoleucine, proline, arginine, lysine, histidine, serine, threonine, aspartic acid, asparagine, cystine, methionine, ornithine, norleucine, phenylalanine, tyrosine, tryptophan, β-alanine, homoserine, homoarginine, isoglutamine, pyroglutamic acid, γ-aminobutryic acid, citrulline, sarcosine, and statine.

3. The compound of claim 1 wherein Xxx is selected from the group of amino acids consisting of glycine, alanine, valine, leucine, isoleucine, proline, arginine, lysine, histidine, threonine, aspartic acid, asparagine, cystine, methionine, ornithine, norleucine, phenylalanine, tyrosine, tryptophan, β-alanine, and homoserine.

4. The compound of claim 1 wherein Xxx is selected from the group of amino acids consisting of glycine, alanine, valine, leucine, isoleucine, proline, arginine, lysine, histidine, threonine, aspartic acid, asparagine, methionine, phenylalanine, tyrosine, serine and tryptophan.

5. The compound of claim 1 wherein Xxx is selected from the group of amino acids consisting of glycine, alanine, valine, leucine, isoleucine, proline, arginine, lysine, histidine, threonine, aspartic acid, asparagine, methionine, phenylalanine, tyrosine, and tryptophan.

6. The compound of claim 1 wherein Xxx is a side-group protected amino acid.

7. The compound of claim 6 wherein Xxx is selected from the group of amino acids consisting of arginine, lysine, aspartic acid, aspargine, serine, histidine, and tyrosine.

8. The compound of claim 6 wherein said amino acid is protected with a t-butyl-type protecting group or a benzyl-type protecting group.

9. The compound of claim 1 which is selected from the group consisting of
Bpoc-Gly-Pfp; Bpoc-Ala-Pfp; Bpoc-Val-Pfp; Bpoc-Ile-Pfp; Bpoc-Leu-Pfp; Bpoc-Pro-Pfp; Bpoc-Met-Pfp;Bpoc-Phe-Pfp; Bpoc-Trp-Pfp; Bpoc-Thr(tBu)-Pfp; Bpoc-Lys(Tfa)-Pfp; Bpoc-Asp(tBu)-Pfp; Bpoc-Asn(Trt)-Pfp; Bpoc-Gln(Trt)-Pfp; Bpoc-His(Trt)-Pfp; Bpoc-Arg(Pmc)-Pfp; Bpoc-Tyr(Allyl)-Pfp; Bpoc-Cys(tBu-thio)-Pfp; and Bpoc-Ser(tBu)-Pfp.

10. The compound of claim 1 which is selected from the group consisting of
Bpoc-Gly-Pfp; Bpoc-Ala-Pfp; Bpoc-Val-Pfp; Bpoc-Ile-Pfp; Bpoc-Leu-Pfp; Bpoc-Pro-Pfp; Bpoc-Met-Pfp;Bpoc-Phe-Pfp; Bpoc-Trp-Pfp; Bpoc-Thr(tBu)-Pfp; Bpoc-Lys(Tfa)-Pfp; Bpoc-Asp(tBu)-Pfp; Bpoc-Asn(Trt)-Pfp; Bpoc-Gln(Trt)-Pfp; Bpoc-His(Trt)-Pfp; Bpoc-Arg(Pmc)-Pfp; Bpoc-Tyr(Allyl)-Pfp; and Bpoc-Cys(tBu-thio)-Pfp.

11. The compound of claim 1 which is selected from the group consisting of
Bpoc-Gly-ODhbt; Bpoc-Ala-ODhbt; Bpoc-Val-ODhbt; Bpoc-Ile-ODhbt; Bpoc-Leu-ODhbt; Bpoc-Pro-ODhbt; Bpoc-Met-ODhbt;Bpoc-Phe-ODhbt; Bpoc-Trp-ODhbt; Bpoc-Thr(tBu)-ODhbt;Bpoc-Lys(Tfa)-ODhbt; Bpoc-Asp(tBu)-ODhbt; Bpoc-Asn(Trt)-ODhbt; Bpoc-Gln(Trt)-ODhbt; Bpoc-His(Trt)-ODhbt; Bpoc-Arg(Pmc)-ODhbt; Bpoc-Tyr(Allyl)-ODhbt; Bpoc-Cys(tBu-thio)-ODhbt, Bpoc-Glu(tBu)-ODhbt and Bpoc-Ser(tBu)-ODhbt.

12. The compound of claim 1 which is selected from the group consisting of
Bpoc-Gly-ODhbt; Bpoc-Ala-ODhbt; Bpoc-Val-ODhbt; Bpoc-Leu-ODhbt; Bpoc-Pro-ODhbt; Bpoc-Phe-ODhbt; Bpoc-Trp-ODhbt; Bpoc-Thr(tBu)-ODhbt; Bpoc-Lys(Tfa)-ODhbt; Bpoc-Asp(tBu)-ODhbt; Bpoc-Asn(Trt)-ODhbt; Bpoc-Gln(Trt)-ODhbt; Bpoc-His(Trt)-ODhbt; Bpoc-Arg(Pmc)-ODhbt; Bpoc-Tyr(Allyl)-ODhbt; Bpoc-Glu(tBu)-ODhbt and Bpoc-Ser(tBu)-ODhbt.

13. A compound of claim 1 which is crystalline and storage stable.

14. A crystalline, storage stable compound according to claim 13 which is selected from the group consisting of:
Bpoc-Gly-Pfp; Bpoc-Ala-Pfp; Bpoc-Val-Pfp; Bpoc-Ile-Pfp; Bpoc-Leu-Pfp; Bpoc-Pro-Pfp; Bpoc-Met-Pfp; Bpoc-Phe-Pfp; Bpoc-Trp-Pfp; Bpoc-Thr(tBu)-Pfp; Bpoc-Lys-(Tfa)-

Pfp; Bpoc-Asp(tBu)-Pfp; Bpoc-Asn-(Trt)-Pfp; Bpoc-Gln(Trt)-Pfp; Bpoc-His(Trt)-Pfp; Bpoc-Arg(Pmc)Pfp; Bpoc-Tyr(Allyl)Pfp; and Bpoc-Cys(tBu-thio)-Pfp.

15. A $N^\alpha$-2(p-biphenyl)-propyloxycarbonyl amino acid pentafluoro ester wherein the amino acid is a side-group protected glutamine or asparagine.

16. The pentafluoro ester of claim 15 wherein the side-group of the glutamine or asparagine is protected with a trityl group.

17. The compound of claim 15 wherein said amino acid is asparagine or glutamine and said side-group protecting agent is selected from the group consisting of a trityl group, a 9-xanthenyl group, a 2,4,6-trimethoxybenzyl group, a 4,4'-dimethylbenzhydral group and a 2,2', 4,4'-tetramethoxybenzhydral group.

18. A 3,4-dihydro-4-oxo-1,2,3-benzotriazin-3-yl ester of a $N^\alpha$-2(p-biphenyl)-propyloxycarbonyl amino acid.

19. The compound of claim 18 which can be represented as:
Bpoc-Xxx-ODhbt
where Xxx is an amino acid.

20. The compound of claim 19 wherein Xxx is selected from the group of amino acids consisting of glycine, alanine, valine, leucine, isoleucine, proline, arginine, lysine, histidine, serine, threonine, aspartic acid, glutamic acid, asparagine, glutamine, cysteine, cystine, methionine, ornithine, norleucine, phenylalanine, tyrosine, tryptophan, β-alanine, homoserine, homoarginine, isoglutamine, pyroglutamic acid, γ-aminobutryic acid, citrulline, sarcosine, and statine.

21. The compound of claim 19 wherein Xxx is selected from the group of amino acids consisting of glycine, alanine, valine, leucine, isoleucine, proline, arginine, lysine, histidine, serine, threonine, aspartic acid, glutamic acid, asparagine, glutamine, cysteine, cystine, methionine, ornithine, norleucine, phenylalanine, tyrosine, tryptophan, β-alanine and homoserine.

22. The compound of claim 19 wherein Xxx is selected from the group of amino acids consisting of glycine, alanine, valine, leucine, isoleucine, proline, arginine, lysine, histidine, threonine, aspartic acid, glutamic acid, asparagine, glutamine, cysteine, methionine, phenylalanine, tyrosine, serine and tryptophan.

23. The compound of claim 18 wherein Xxx is selected from the group of amino acids consisting of glycine, alanine, valine, leucine, isoleucine, proline, arginine, lysine, histidine, threonine, aspartic acid, glutamic acid, asparagine, glutamine, cysteine, methionine, phenylalanine, tyrosine, serine and tryptophan.

24. The compound of claim 18 wherein Xxx is a side-group protected amino acid.

25. The compound of claim 24 wherein Xxx is selected from the group of amino acids consisting of arginine, lysine, aspartic acid, asparagine, glutamic acid, glutamine, histidine, cysteine, ornithine, and tyrosine.

26. The compound of claim 25 wherein said amino acid is protected with a t-butyl-type protecting group or a benzyl-type protecting group.

27. The compound of claim 18 wherein said amino acid is asparagine or glutamine and said side-group protecting group is selected from the group consisting of a trityl group, a 9-xanthenyl group, a 2,4,6-trimethoxybenzyl group, a 4,4'-dimethylbenzhydral group and a 2,2', 4,4'-tetramethoxybenzhydral group.

28. A compound of the formula:

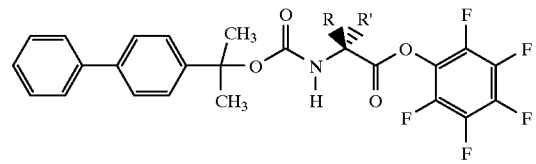

wherein R and R', independently of one another, are selected from the group consisting of hydrogen, alkyl, cycloalkyl, substituted cycloalkyl, aryl and substituted aryl except that the compound is not $N^\alpha$-2(p-biphenyl)-propyloxycarbonyl-L-glutamine pentafluorophenyl ester, $N^\alpha$-2(p-biphenyl)-propyloxycarbonyl-t-butyl-L-glutamate pentafluorophenyl esters, or $N^\alpha$-2(p-biphenyl-propyloxycarbonyl-S-(acetamidomethyl)-L-cysteine pentafluorophenyl ester.

29. The compound of claim 28 wherein one of R or R' is hydrogen.

30. A compound having the formula:

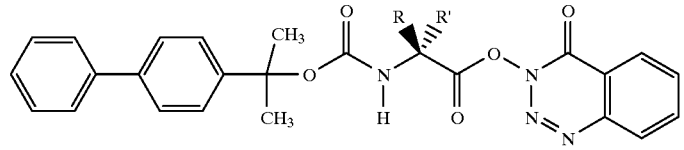

wherein R and R', independently of one another, are selected from the group consisting of hydrogen, alkyl, cycloalkyl, substituted cycloalkyl, aryl and substituted aryl groups.

31. The compound of claim 30 wherein one of R or R' is hydrogen.

32. In a method for the synthesis of a polypeptide chain which comprises the steps of deprotecting an N-protected amino acid component and reacting said deprotected amino acid component with an activated N-protected amino acid reagent, the improvement wherein said activated N-protected amino acid reagent is a pentafluorophenyl ester or a 3,4-dihydro-4-oxo-1,2,3-benzotriazin-3-yl ester of a $N^\alpha$-2(p-biphenyl)-propyloxycarbonyl amino acid.

33. The method of claim 32 wherein said activated N-protected amino acid reagent is an $N^\alpha$-2(p-biphenyl)-propyloxycarbonyl amino acid pentafluorophenyl ester.

34. The method of claim 33 wherein said activated N-protected amino acid reagent is an $N^\alpha$-2(p-biphenyl)-propyloxycarbonyl amino acid 3,4-dihydro-4-oxo-1,2,3-benzotriazine-3-yl ester.

35. The method of claim 32 in which the polypeptide chain is synthesized on an insoluble solid support and wherein said N-protected amino acid component is coupled to said insoluble support.

36. The method of claim 35 wherein said insoluble support is a phenyl ester-type resin.

37. The method of claim 36 wherein said resin is one with oxime or thioester linkages.

38. The method of claim 32 wherein said resin is one with an allyl ester-type linker.

39. The method of claim 32 wherein said N-protected amino acid component is protected with an $N^\alpha$-2(p-biphenyl)-propyloxycarbonyl group.

40. The method of claim 39 wherein said $N^\alpha$-2(p-biphenyl)-propyloxycarbonyl-protected amino acid component is deprotected using a deprotecting agent that is a dilute solution of trifluoroacetic acid.

41. The method of claim 40 wherein said deprotecting agent is a dilute solution of trifluoroacetic acid in dichloromethane.

42. The method of claim 39 wherein said $N^\alpha$-2(p-biphenyl)-propyloxycarbonyl-protected amino acid component is deprotected using a deprotecting agent that is a solution of glacial acetic acid.

* * * * *

UNITED STATES PATENT AND TRADEMARK OFFICE
CERTIFICATE OF CORRECTION

PATENT NO. : 5,952,497

DATED : Sep. 14, 1999

INVENTOR(S) : Carey

It is certified that error appears in the above-identified patent and that said Letters Patent is hereby corrected as shown below:

In columns 7 and 8, Formula 4, please delete

"

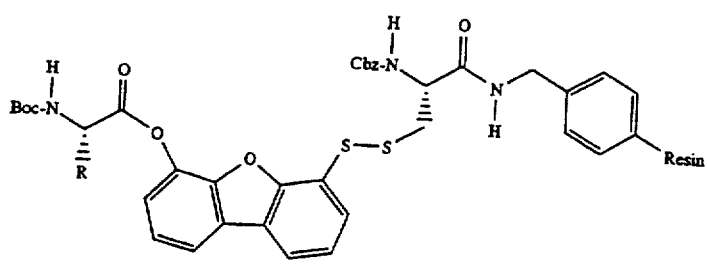

"

and replace it with

--

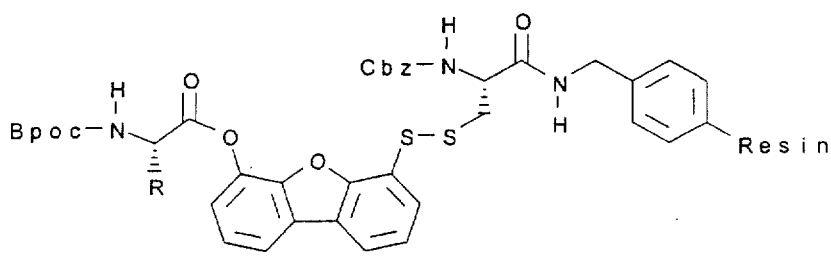

--

UNITED STATES PATENT AND TRADEMARK OFFICE
CERTIFICATE OF CORRECTION

PATENT NO.    :   5,952,497

DATED         :   Sep. 14, 1999

INVENTOR(S)   :   Carey

It is certified that error appears in the above-identified patent and that said Letters Patent is hereby corrected as shown below:

At column 8, line 61, please delete the first occurrence of "$N^\alpha$-Bpoc" and replace it with --$N^\alpha$-Boc--.

At column 8, line 61, please delete the second occurrence of "$N^\alpha$-Bpoc" and replace it with --$N^\alpha$-Fmoc--.

Signed and Sealed this

Twenty-fourth Day of October, 2000

Attest:

Q. TODD DICKINSON

*Attesting Officer*      *Director of Patents and Trademarks*